US012626819B2

(12) United States Patent　　　　(10) Patent No.:　US 12,626,819 B2
Gee et al.　　　　　　　　　　　　　(45) Date of Patent:　May 12, 2026

(54) MACHINE LEARNING MODELS FOR DETECTING OUTLIERS AND ERRONEOUS SENSOR USE CONDITIONS AND CORRECTING, BLANKING, OR TERMINATING GLUCOSE SENSORS

(71) Applicant: MEDTRONIC MINIMED, INC., Northridge, CA (US)

(72) Inventors: Elaine Gee, Windsor, CA (US); Jeffrey Nishida, Chicago, IL (US); Peter Ajemba, Canyon Country, CA (US); Keith Nogueira, Mission Hills, CA (US); Andrea Varsavsky, Santa Monica, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 1070 days.

(21) Appl. No.: 17/163,186

(22) Filed: Jan. 29, 2021

(65) Prior Publication Data

US 2022/0189631 A1　　Jun. 16, 2022

Related U.S. Application Data

(63) Continuation of application No. 17/121,624, filed on Dec. 14, 2020, now abandoned.

(51) Int. Cl.
*G16H 50/20*　　　(2018.01)
*G06N 20/00*　　　(2019.01)
*G16H 40/63*　　　(2018.01)

(52) U.S. Cl.
CPC ............. *G16H 50/20* (2018.01); *G06N 20/00* (2019.01); *G16H 40/63* (2018.01)

(58) Field of Classification Search
CPC ........ G16H 50/20; G16H 40/63; G06N 20/00; A61B 2560/028; A61B 5/1495; A61B 5/7203; A61B 5/7264; A61B 5/14532; A61B 5/14503; A61B 5/1473; A61B 5/7221; A61B 5/7267; A61B 5/746
See application file for complete search history.

(56) References Cited

U.S. PATENT DOCUMENTS

| | | |
|---|---|---|
| 4,562,751 A | 1/1986 | Nason et al. |
| 4,573,994 A | 3/1986 | Fischell et al. |
| 4,678,408 A | 7/1987 | Nason et al. |
| 4,685,903 A | 8/1987 | Cable et al. |
| 4,755,173 A | 7/1988 | Konopka et al. |
| 5,391,250 A | 2/1995 | Cheney, II et al. |
| 5,482,473 A | 1/1996 | Lord et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |

(Continued)

FOREIGN PATENT DOCUMENTS

| | | |
|---|---|---|
| CN | 105403705 A | 3/2016 |
| CN | 108937954 A | 12/2018 |

(Continued)

OTHER PUBLICATIONS

Code of Federal Regulations: A point in time eCFR system, Title 21, Chapter I, Subchapter H, Part 862, Subpart B (21 CFR 862.1355), pp. 1-3. URL: https://www.ecfr.gov/current/title-21/chapter-I/subchapter-H/part-862/subpart-B/section-862.1355. [retrieved Nov. 18, 2022].

Freckmann, G. et al., "Measures of Accuracy for Continuous Glucose Monitoring and Blood Glucose Monitoring Devices", Journal of Diabetes Science and Technology, May 2019, vol. 13, No. 3, 575-583. DOI: 10.1177/1932296818812062.

Extended European Search Report issued in corresponding application EP 21212472.1 dated May 23, 2022 (8 pages).

U.S. Non-Final Office Action dated Apr. 3, 2024 in U.S. Appl. No. 17/121,624.

U.S. Final Office Action dated Oct. 22, 2024 in U.S. Appl. No. 17/121,624.

(Continued)

*Primary Examiner* — Soren Harward
*Assistant Examiner* — Dawn Bickham
(74) *Attorney, Agent, or Firm* — Weaver Austin Villeneuve & Sampson LLP

(57) ABSTRACT

Techniques for improving continuous glucose monitoring ("CGM") are described herein. In some embodiments, the techniques involve obtaining sensor data; applying, to the sensor data, a machine learning model trained to identify sensor data error patterns; and detecting an erroneous sensor use condition based on output of the machine learning model indicating an error pattern identified in the sensor data.

18 Claims, 13 Drawing Sheets

(56) References Cited

U.S. PATENT DOCUMENTS

| | | | |
|---|---|---|---|
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Memoe et al. |
| 2009/0168832 A1 | 7/2009 | Bauerle |
| 2010/0160861 A1 | 6/2010 | Causey, III et al. |
| 2015/0351673 A1* | 12/2015 | Vanslyke ............. A61B 5/1473 |
| | | 600/301 |
| 2017/0185733 A1* | 6/2017 | Nogueira ............. A61B 5/1495 |
| 2017/0311897 A1* | 11/2017 | Faccioli ............... A61B 5/7203 |
| 2018/0185733 A1 | 7/2018 | King |
| 2019/0076066 A1 | 3/2019 | Ajemba et al. |
| 2021/0110313 A1 | 4/2021 | Jones |
| 2022/0189630 A1 | 6/2022 | Gee et al. |
| 2022/0254492 A1* | 8/2022 | Armitage ............... G16H 50/30 |

FOREIGN PATENT DOCUMENTS

| | | |
|---|---|---|
| CN | 110448306 A | 11/2019 |
| CN | 110785816 A | 2/2020 |

OTHER PUBLICATIONS

CN Office Action dated Nov. 12, 2025 in CN Application No. 202111520115.X, with English Translation.

* cited by examiner

100

150

500

555

590 Signal Processor

595 Measurement Processor

597 Display or Transmission

585 Regulator

580 Power Supply

575

570

565

Sensor Electronics Device
560

550

555

575

570

565

531

I/F Converter
530

Digital-to-Analog Converter 520

Microcontroller
510

Sensor Electronics Device
560

700

800

MACHINE LEARNING MODELS FOR DETECTING OUTLIERS AND ERRONEOUS SENSOR USE CONDITIONS AND CORRECTING, BLANKING, OR TERMINATING GLUCOSE SENSORS

RELATED APPLICATION DATA

This application is a continuation of U.S. patent application Ser. No. 17/121,624, filed Dec. 14, 2020, which is incorporated herein by reference in its entirety.

FIELD

The present technology is generally related to sensor technology, including sensors used for sensing a variety of physiological parameters, e.g., glucose concentration.

BACKGROUND

Over the years, a variety of sensors have been developed for detecting and/or quantifying specific agents or compositions in a patient's blood, which enable patients and medical personnel to monitor physiological conditions within the patient's body. Illustratively, subjects may wish to monitor blood glucose levels in a subject's body on a continuing basis. Thus, glucose sensors have been developed for use in obtaining an indication of blood glucose levels in a diabetic patient. Such readings are useful in monitoring and/or adjusting a treatment regimen which typically includes the regular administration of insulin to the patient. Presently, a patient can measure his/her blood glucose ("BG") using a BG measurement device (i.e., glucose meter), such as a test strip meter, a continuous glucose measurement system (or a continuous glucose monitor), or a hospital BG test. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device.

SUMMARY

Current continuous glucose monitoring ("CGM") systems use CGM calibration algorithms to determine when measurements are accurate. For example, accuracy may change based on wear, battery life, and other factors. Current CGM systems determine accuracy based on an independent input signal, whereas systems and methods described herein utilize a multi-dimensional input signal for determining accuracy. The multi-dimensional input signal may include an Interstitial Current Signal ("Isig"), an Electrochemical Impedance Spectroscopy Signal ("EIS"), a counter voltage ("Vcntr"), and/or other signals. The multi-dimensional input signal improves CGM performance, leading to more reliable determinations of accuracy, wear, battery life, and other factors and providing a user with more accurate data.

Though the use of a multi-dimensional input signal improves CGM performance, present CGM requirements are difficult to scale with the multi-dimensional inputs. Government agencies (e.g., the Federal Drug Administration ("FDA")) impose restrictions and requirements for the sensitivity and accuracy of CGMs. For example, CGM devices are required to meet numerous criteria (e.g., FDA's integrated continuous glucose monitoring ("iCGM") criteria) in order for the sensor data to be considered accurate enough to qualify for preferential treatment during regulatory the regulatory approval process. The iCGM criteria is designed to characterize the relative distribution of error of a CGM system to balance the often-competing needs of an overall mean error value and short tails in the error distribution. In addition, current systems used as predicate devices in fashioning the iCGM criteria are based on single signal analysis, so the criteria may be difficult to generalize to systems based on multi-dimensional input signals as described herein. To solve these problems, methods, systems, and devices described herein may train a machine learning model to classify multi-dimensional input signals in accordance with the iCGM criteria. The outputs from the trained machine learning model may be used to blank (i.e., remove, ignore) measurements, during computation within a glucose estimation device, which do not meet the iCGM criteria. Thus, the methods, systems, and devices described herein allow for improved CGM techniques that are compatible with the FDA's iCGM criteria and related criteria designed to balance gross measures of accuracy with error distributions featuring shorter tail.

More particularly, the methods, systems, and devices describe training a machine learning model to identify outlier measurements based on behavior signatures and informed by the iCGM and similar criteria. The machine learning model may take as inputs multi-dimensional CGM sensor data and may use training data to set model parameters. The training data may include clinical data on iCGM performance. In some embodiments, the system may classify the training data according to known classifications (e.g., large negative bias, large positive bias, nominal accuracy, poor accuracy, intermediate accuracy, good accuracy, or other classifications). The system may receive multi-dimensional CGM sensor data from a sensor electrode or another computing device and may input the sensor data into the machine learning model it contains or contained in another computing device. Outputs from the machine learning model may indicate whether the CGM sensor data corresponds to an outlier (e.g., or to a known classification, as described above) or fits a known pattern associated with an error state or error condition. If the CGM sensor data corresponds to an outlier, the system may not process the corresponding sensor data or may blank or not display the sensor data on a display interface of a user's device. In some examples, the system may blank sensor data by foregoing to transmit the sensor data to a user device or any other device with a display interface.

Another limitation of current systems is a loss of data due to blanking. For example, if a sensor device is consistently blanking, the quantity of data processed by the device or received by a user of the sensor device may be inadequate. Accordingly, methods, systems, and devices described herein may terminate the sensor device (e.g., stop transmitting sensor data from that sensor device) based on determining that a certain number of outlier measurements has been reached or a certain number of blanking instances has been activated during a specified period during sensor wear. More particularly, the methods, systems, and devices describe using an outlier counter (e.g., or a buffer, threshold, or any other means) to track outlier measurements. For example, the system may reset the outlier counter (e.g., to zero) upon determining that a sensor datapoint does not correspond to an outlier measurement (e.g., as determined by the machine learning model). The system may increment the outlier counter for each datapoint that is classified as an outlier by the machine learning model. The system may use various additional criteria in conjunction with the outlier counter (e.g., or other means for tracking outlier measurements). For example, the outlier counter may track a number of outlier measurements that are received consecutively, in a certain time period, or within any other constraints. Once the outlier counter breaches (e.g., meets or exceeds) a threshold, the system may terminate the sensor device. In some embodiments, the system may alert the user that the sensor device must be replaced.

In some aspects, methods, systems, and devices for continuous glucose monitoring are described. For example, the system may retrieve a machine learning model that is trained to identify outlier measurements based on iCGM criteria using training data. In some embodiments, the training data may include clinical data on iCGM performance. The system may receive CGM sensor data and input the sensor data into the machine learning model. The system may receive an output from the machine learning model indicating that the sensor data corresponds to an outlier measurement. Based on the output, the system may blank (e.g., ignore, eschew from transmitting to another device) or not display the sensor data (e.g., on a display interface) on a user device.

Another limitation of conventional continuous glucose monitoring ("CGM") systems is inability to dynamically detect and correct errors in the sensor data. CGM systems continuously present sensor data for a user of a sensor device. The system must therefore process and respond to characteristics of the sensor data in real-time. Notably, any error in this data may result in severe or even fatal effects to the user. Moreover, conventional CGM systems lack the functionality to detect and correct for errors in the data as they arise. Systems and methods described herein train a machine learning model to detect error patterns in the sensor data. For example, the system may train the machine learning model to recognize error pattern characteristics and identify underlying erroneous sensor use conditions. However, conventional pattern recognition technology would be unsuccessful at identifying erroneous sensor use conditions associated with error patterns in the sensor data, as pattern recognition alone is insufficient for understanding the complexities of the sensor data surrounding the error patterns. Systems and methods described herein thus rely upon context information relating to the sensor data in order to determine the erroneous sensor use condition. For example, the system relies upon historic information relating to the sensor data, such as behaviors, trends, and patterns of the sensor data within a time period. The behaviors, trends, and patterns of the sensor data allow the system to identify between identical error patterns that are associated with different erroneous sensor use conditions. Additionally, the system accounts for behaviors and patterns of the various sensor input features that make up the sensor data. Identifying the correct erroneous sensor use condition associated with the detected error pattern is essential for correcting the error. Once the system has identified the correct erroneous sensor use condition, the system may determine a viable resolution for correcting the error in the data.

In order to comply with the iCGM criteria, the CGM system must ensure that sensor data which does not comply with the iCGM criteria is not shown to the user. With current systems, this leads to excessive blanking in response to abnormal sensor data. Such excessive blanking may deprive a user of a sensor device of valuable sensor glucose data. Systems and methods described herein improve upon current systems by detecting and correcting for errors in complex sensor data in real time in order to maximize the accurate data that the system is able to provide to the user in compliance with iCGM criteria.

More particularly, methods, systems, and devices for continuous glucose monitoring are described. For example, the system may retrieve a machine learning model that is trained to identify erroneous sensor use conditions based on sensor data error patterns using training data. In some embodiments, the training data may include clinical data on erroneous sensor use conditions. The system may receive CGM sensor data and input the sensor data into the machine learning model. The system may receive an output from the machine learning model indicating an erroneous sensor use condition based on an error pattern identified in the sensor data. Based on the output, the system may determine and implement a resolution in order to correct the identified erroneous sensor use condition.

Various other aspects, features, and advantages will be apparent through the detailed description and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a sub-part of, or the entirety of, a given item (e.g., data) unless the context clearly dictates otherwise.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A detailed description of embodiments of the invention will be made with reference to the accompanying drawings, wherein like numerals designate corresponding parts in the figures.

5

Figure 8:
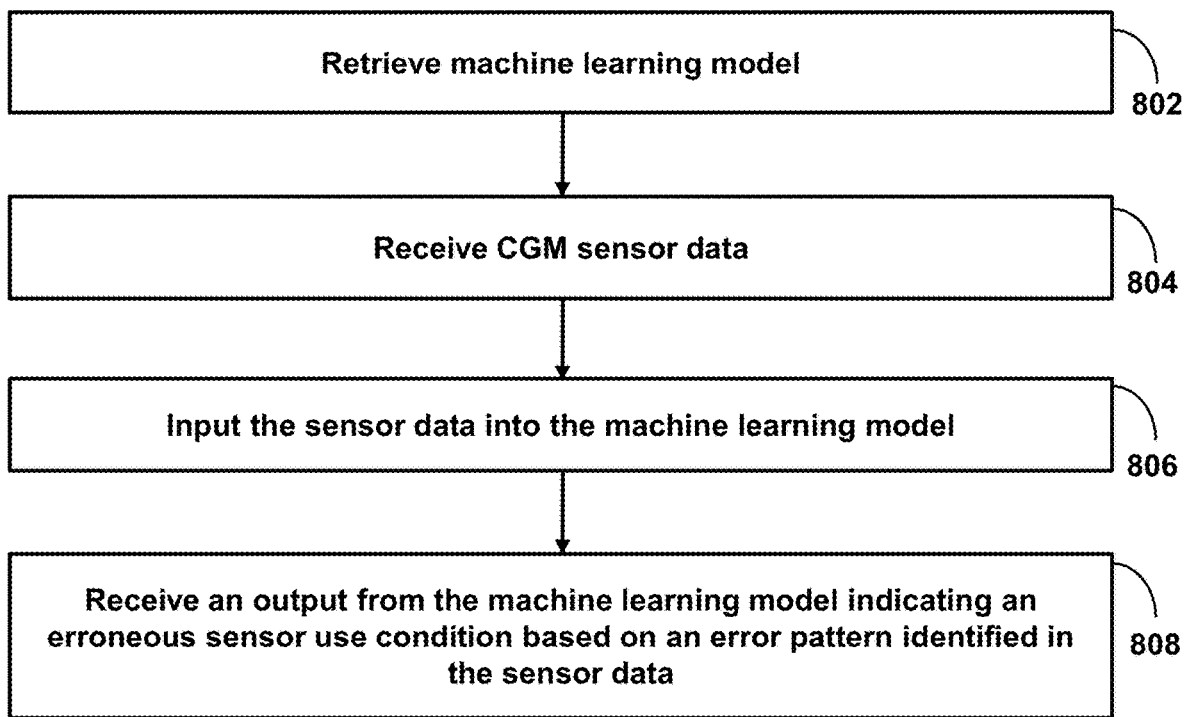

FIG. 8 shows a flowchart of the steps involved in applying machine learning models to detect and correct for erroneous sensor use conditions, in accordance with one or more embodiments.

Figure 9:
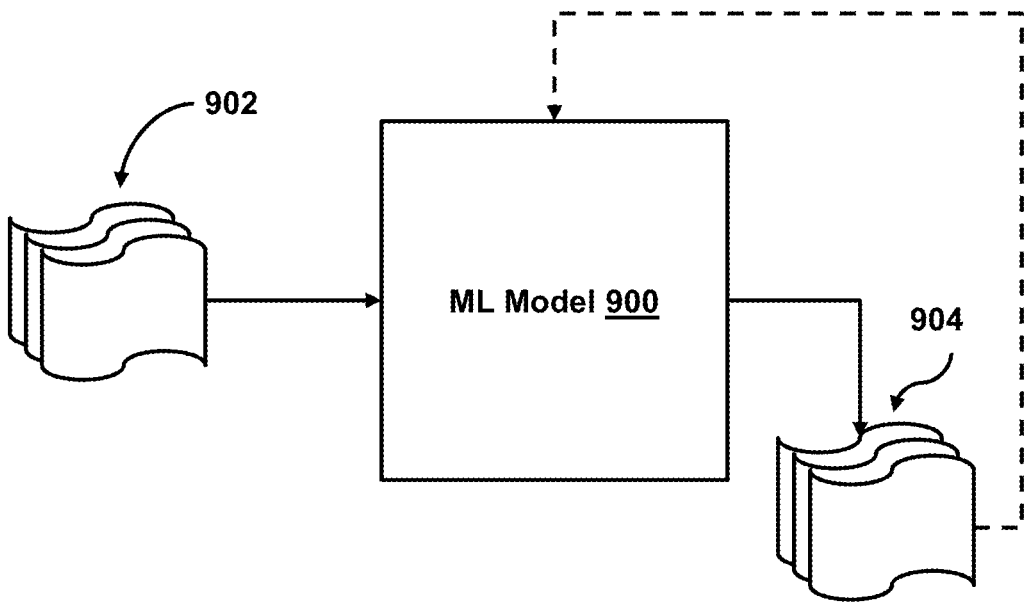

FIG. 9 shows a machine learning model system for making predictions that facilitate both classification of outlier measurements based on iCGM criteria and detection and correction of erroneous sensor use conditions, in accordance with one or more embodiments.

Figure 10:
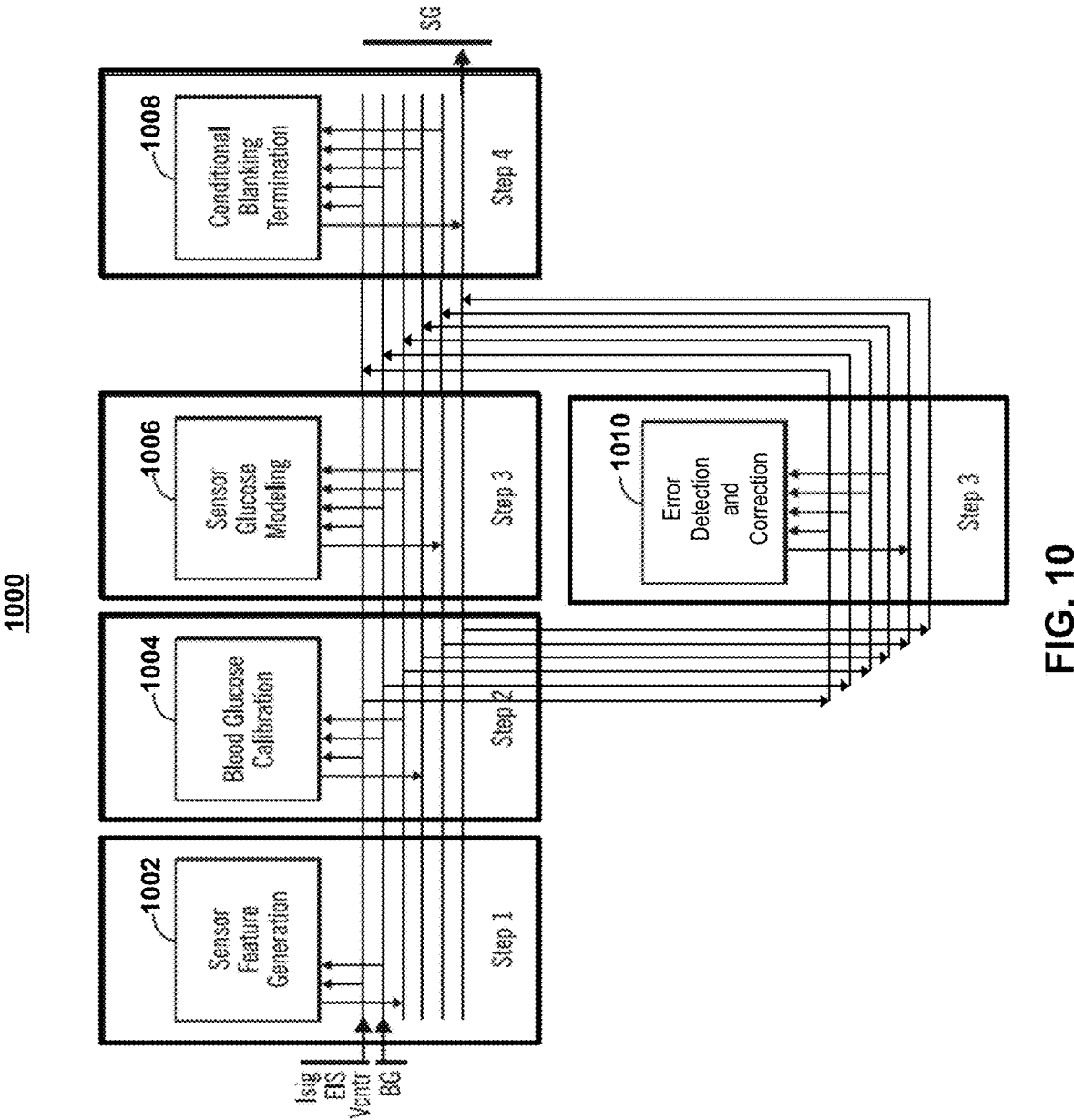

FIG. 10 shows a flow diagram for conditional blanking and termination and error detection and correction, in accordance with one or more embodiments.

Figure 11:
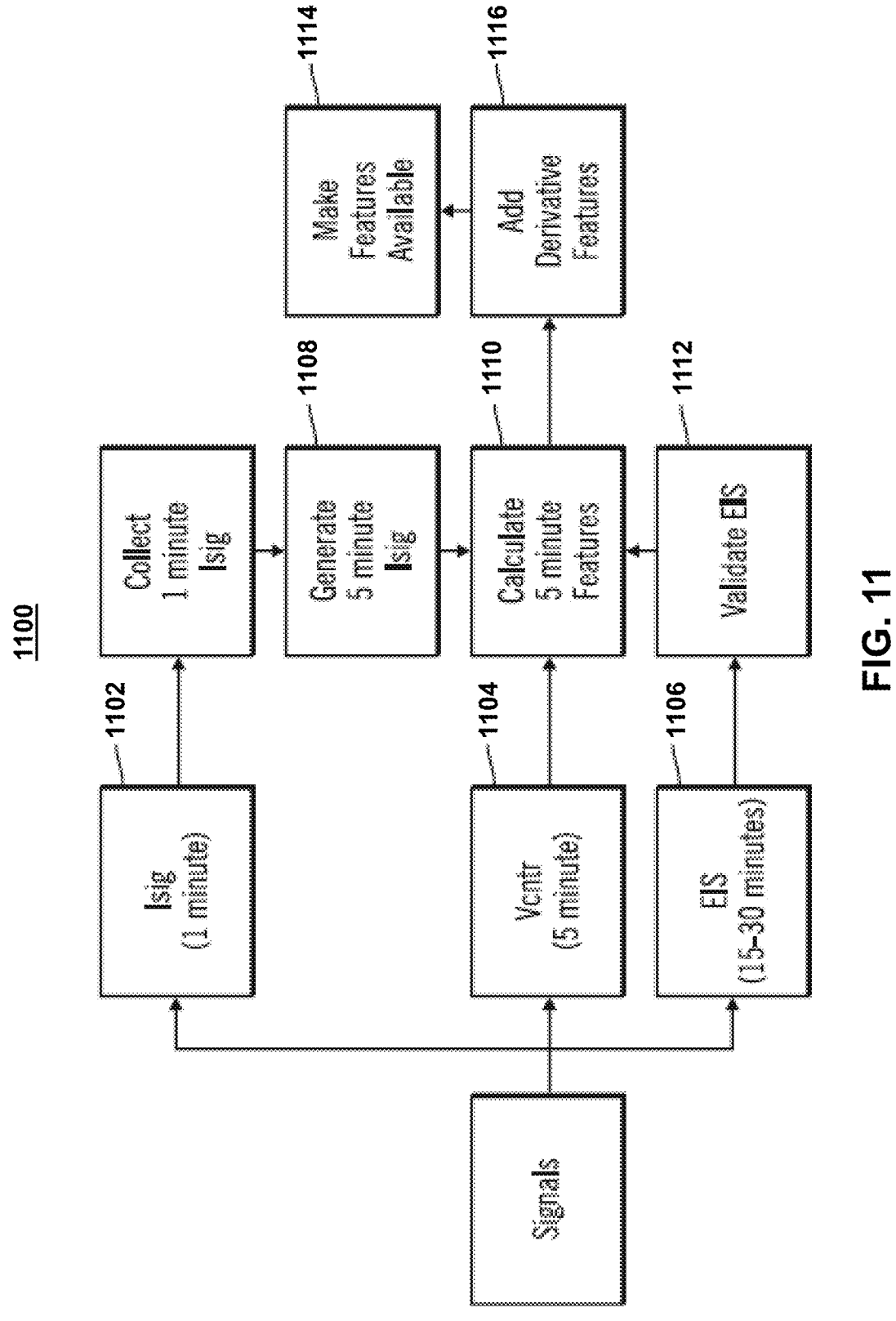

FIG. 11 shows a schematic of a sensor feature generator of FIG. 10, in accordance with one or more embodiments.

Figure 12:
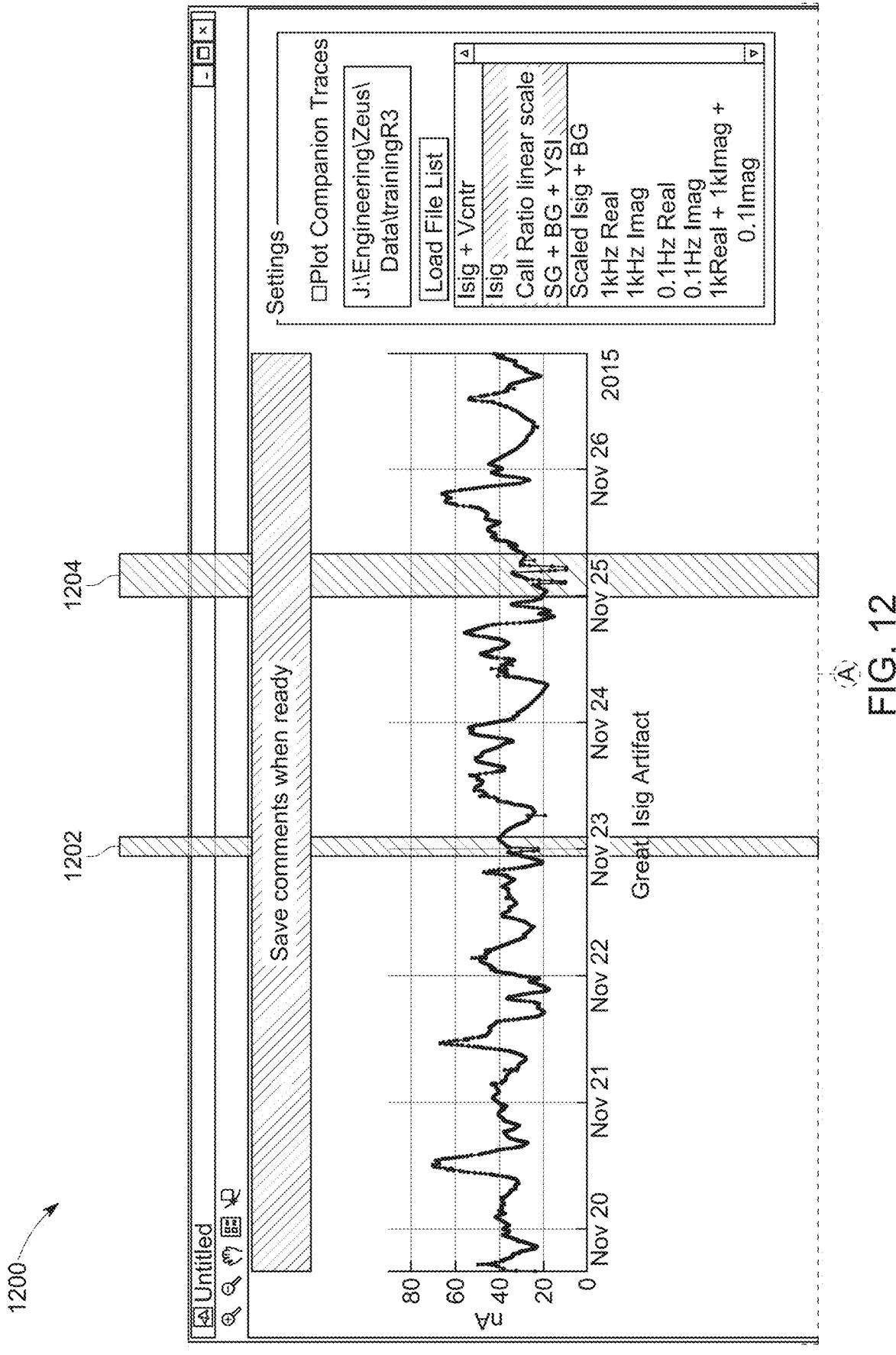
Figure 12:
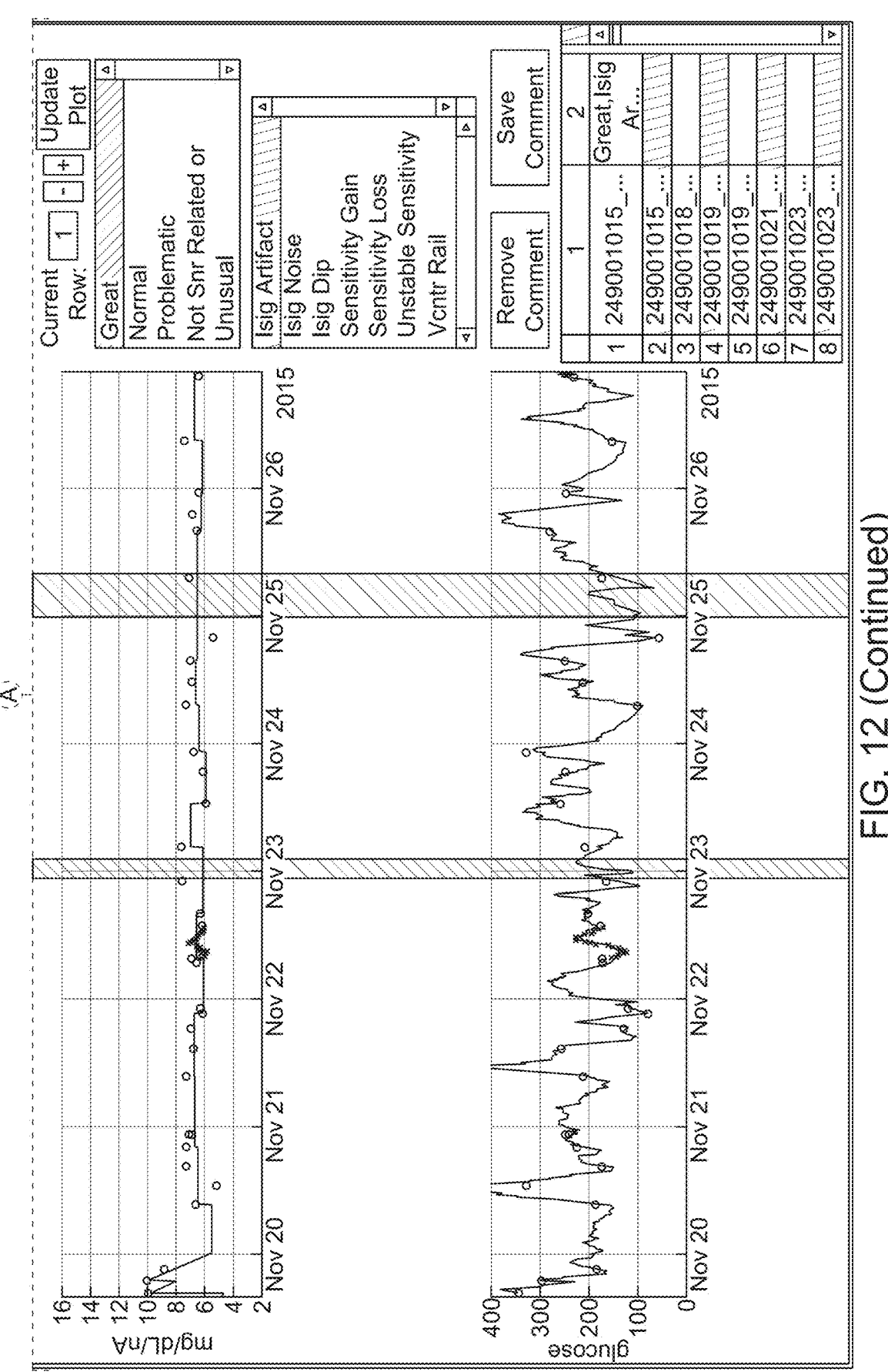

FIG. 12 shows a graph highlighting error patterns in sensor data, in accordance with one or more embodiments.

DETAILED DESCRIPTION

In the following description, reference is made to the accompanying drawings which form a part hereof and which illustrate several embodiments of the present inventions. It is understood that other embodiments may be utilized, and structural and operational changes may be made without departing from the scope of the present inventions.

The inventions herein are described below with reference to flowchart illustrations of methods, systems, devices, apparatus, and programming and computer program products. It will be understood that each block of the flowchart illustrations, and combinations of blocks in the flowchart illustrations, can be implemented by programing instructions, including computer program instructions (as can any menu screens described in the figures). These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein. Programming instructions may also be stored in and/or implemented via electronic circuitry (e.g., storage circuitry, processing circuitry), including integrated circuits (ICs) and Application Specific Integrated Circuits (ASICs) used in conjunction with sensor devices, apparatuses, and systems. The following terms and definitions may also be used herein:

| Term | Definition |
| --- | --- |
| BG | Blood Glucose value in mg/dL typically from a fingerstick reading. Assumed use is for a sensor calibration |

6

-continued

| Term | Definition |
| --- | --- |
| Calibrated Mode | Sensor operation mode in which the algorithm expects to receive BG calibrations as part of regular operation |
| CE | Calibration Error |
| CF (or calFactor) | Calibration Factor, sensor sensitivity to glucose used to calculate sensor glucose. Units are mg/dL/nA |
| CR (or cr) | Calibration Ratio, sensitivity based on a single BG and Isig |
| Discard | Packet flagged to be invalid based on Isig. |
| early calibration | Temporary CF update on the packet following a BG |
| EIS | Electrochemical Impedance Spectroscopy, Diagnostic capability to measure impedances at varying frequencies applied by the AFE IC |
| final calibration | Refers to updates to CF and other variables which may occur 10-15 minutes after a BG entry |
| fisig | Filtered Isig, used in calibration and SG calculation |
| GST | Glucose Sensor Transmitter |
| GOx | Glucose Oxidase |
| initialization | Sensor Initialization. This typically refers to data collection activities during sensor warm up period |
| Instant calibration error | CE check based on prior Isig, determines if a BG can be used for calibration |
| invalid packet | Refers to a packet being flagged as invalid. Packets flagged as invalid do not show SG to the user. |
| Isig | 5-minute reading of sensor current in nA. Sometimes called "raw Isig" |
| Isig1 | 1-minute reading of sensor current in nA. Sometimes called "1-minute Isig" |
| Isig Dip | Isig Dip Calibration. Refers to logic which may adjust CF following a calibration on an abnormally low Isig |
| MAX_CR | Maximum acceptable CR |
| MIN_CR | Minimum acceptable CR |
| Not Calibrated Mode | Sensor operation mode in which the algorithm does not expect to receive BG calibrations as part of regular operations. The algorithm can utilize BG calibrations if any is made available. |
| Packet (or SG Packet or Isig Packet) | Refers to the collection of variables calculated at the 5-minute interval, including Isig, sg, etc. |
| SG | Sensor Glucose value in mg/dL |
| Vset | Voltage potential |

Figure 1:
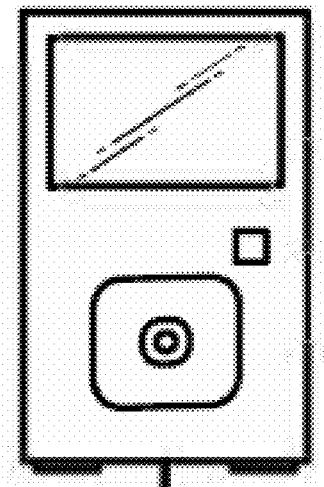
FIG. 1 illustrates wearable sensor electronics devices, in accordance with one or more embodiments.
Figure 1:
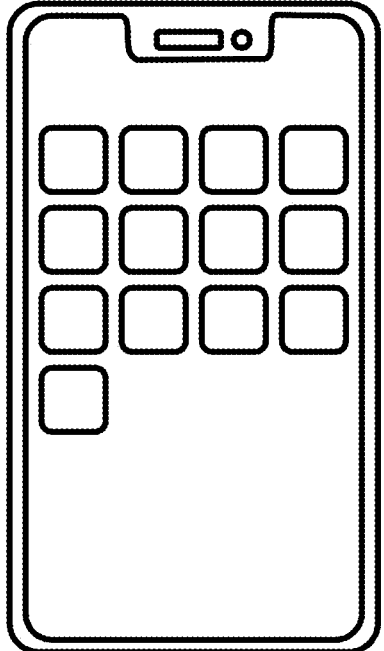

FIG. 1 illustrates wearable sensor electronics devices 100 and 150, in accordance with one or more embodiments. In some embodiments, wearable sensor electronics device 100 may be an infusion pump. In some embodiments, the infusion pump may include a display. In some embodiments, wearable sensor electronics device 100 may be a combination infusion pump/glucose sensor. In some embodiments, wearable sensor electronics device 150 may be a cellular phone or any computing device. In some embodiments, wearable sensor electronics devices 100 and 150 may include a computer, a personal digital assistant, a pager, or any other suitable wearable device. In some embodiments, wearable sensor electronics devices 100 and 150 may house components described below in relation to FIGS. 2-6.

Figure 2:
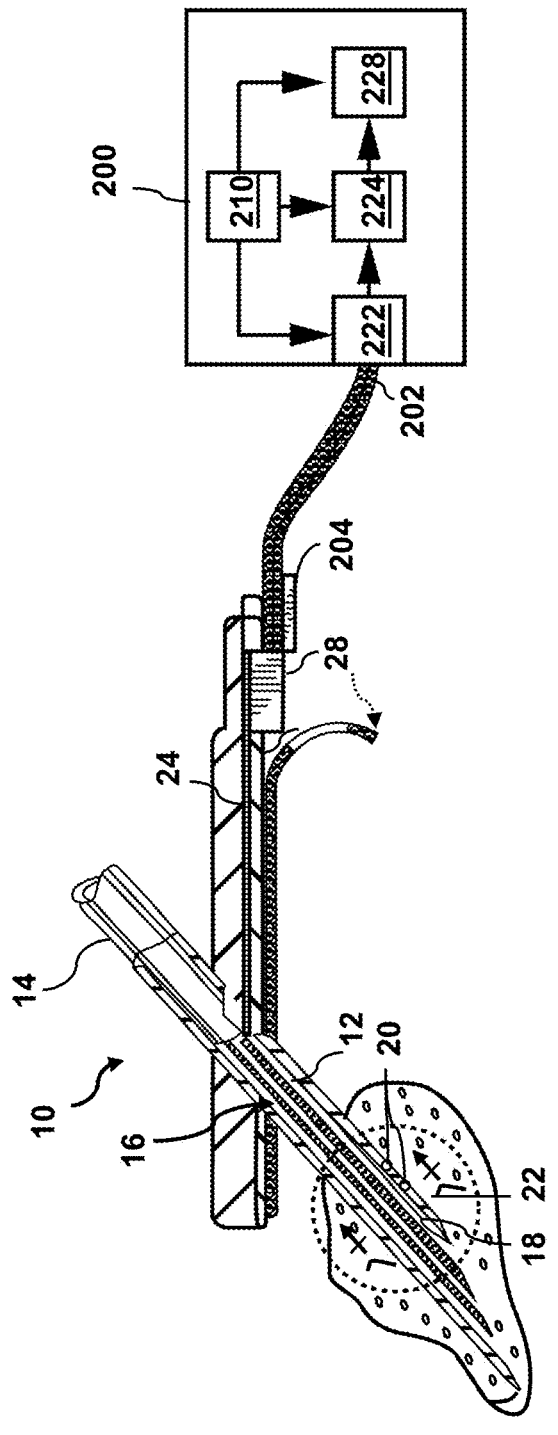
FIG. 2 is a perspective view of a subcutaneous sensor insertion set and block diagram of a sensor electronics device, in accordance with one or more embodiments.

FIG. 2 is a perspective view of a subcutaneous sensor insertion set and a block diagram of a sensor electronics device (e.g., wearable sensor electronics devices 100 or 150, as shown in FIG. 1, or any other suitable sensor electronics device). As illustrated in FIG. 2, a subcutaneous sensor set 10 is provided for subcutaneous placement of an active portion of a flexible sensor 12 (see, e.g., FIG. 3), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In one embodiment, the one or more sensor electrodes 20 may include a counter electrode, a reference electrode, and one or more working electrodes. After insertion, the insertion needle 14 is withdrawn to leave the cannula 16 with the sensing portion 18 and the sensor electrodes 20 in place at the selected insertion site.

In particular embodiments, the subcutaneous sensor set 10 facilitates accurate placement of a flexible thin film electrochemical sensor 12 of the type used for monitoring specific blood parameters representative of a user's condition. The sensor 12 monitors glucose levels in the body and may be used in conjunction with automated or semi-automated medication infusion pumps (e.g., wearable sensor electronics device 100, as shown in FIG. 1) of the external or implantable type to control delivery of insulin to a diabetic patient, as described, e.g., in U.S. Pat. Nos. 4,562,751; 4,678,408; 4,685,903 or 4,573,994, which are herein incorporated by reference.

Particular embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor or sensor electronics device 200 (e.g., wearable sensor electronics devices 100 or 150, as shown in FIG. 1, or any other suitable sensor electronics device) for monitoring a user's condition in response to signals derived from the sensor electrodes 20. Further description of flexible thin film sensors of this general type are to be found in U.S. Pat. No. 5,391,250, entitled METHOD OF FABRICATING THIN FILM SENSORS, which is herein incorporated by reference. The connection portion 24 may be conveniently connected electrically to the monitor or sensor electronics device 200 or by a connector block 28 (or the like) as shown and described in U.S. Pat. No. 5,482,473, entitled FLEX CIRCUIT CONNECTOR, which is also herein incorporated by reference. Thus, in accordance with some embodiments, subcutaneous sensor sets 10 may be configured or formed to work with either a wired or a wireless characteristic monitor system.

The sensor electrodes 20 may be used in a variety of sensing applications and may be configured in a variety of ways. For example, the sensor electrodes 20 may be used in physiological parameter sensing applications in which some type of biomolecule is used as a catalytic agent. For example, the sensor electrodes 20 may be used in a glucose and oxygen sensor having a glucose oxidase (GOx) enzyme catalyzing a reaction with the sensor electrodes 20. The sensor electrodes 20, along with a biomolecule or some other catalytic agent, may be placed in a human body in a vascular or non-vascular environment. For example, the sensor electrodes 20 and biomolecule may be placed in a vein and be subjected to a blood stream or may be placed in a subcutaneous or peritoneal region of the human body.

The monitor 200 may also be referred to as a sensor electronics device 200. The monitor 200 may include a power source 210, a sensor interface 222, processing electronics 224, and data formatting electronics 228. The monitor 200 may be coupled to the sensor set 10 by a cable 202 through a connector that is electrically coupled to the connector block 28 of the connection portion 24. In an alternative embodiment, the cable may be omitted. In this embodiment, the monitor 200 may include an appropriate connector for direct connection to the connection portion 204 of the sensor set 10. The sensor set 10 may be modified to have the connector portion 204 positioned at a different location, e.g., on top of the sensor set to facilitate placement of the monitor 200 over the sensor set.

In one embodiment, the sensor interface 222, the processing electronics 224, and the data formatting electronics 228 are formed as separate semiconductor chips, however, alternative embodiments may combine the various semiconductor chips into a single, or multiple customized semiconductor chips. The sensor interface 222 connects with the cable 202 that is connected with the sensor set 10.

The power source 210 may be a battery. The battery can include three series silver oxide 357 battery cells. In alternative embodiments, different battery chemistries may be utilized, such as lithium-based chemistries, alkaline batteries, nickel metal hydride, or the like, and a different number of batteries may be used. The monitor 200 provides power to the sensor set via the power source 210, through the cable 202 and cable connector 204. In one embodiment, the power is a voltage provided to the sensor set 10. In another embodiment, the power is a current provided to the sensor set 10. In an embodiment, the power is a voltage provided at a specific voltage to the sensor set 10.

Figure 3:
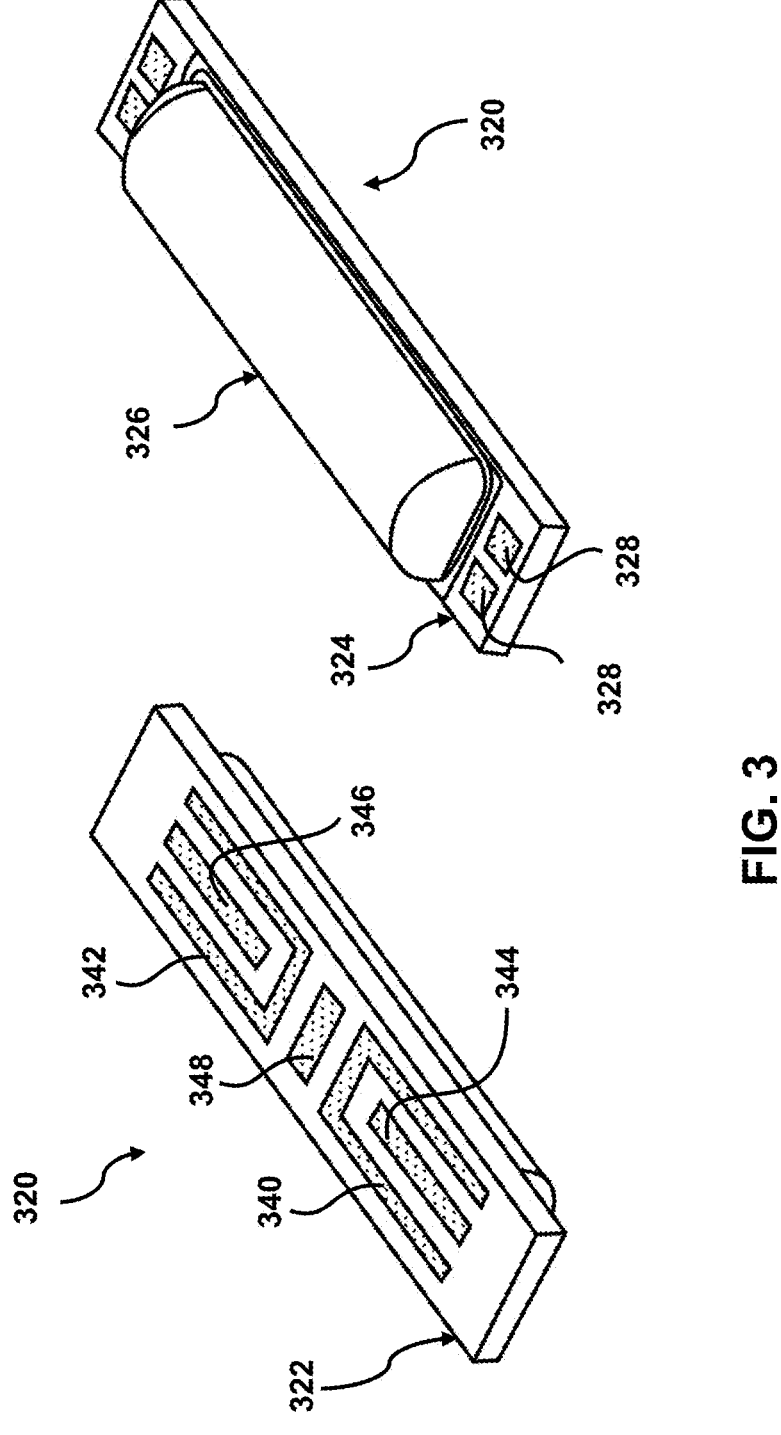
FIG. 3 illustrates a substrate having two sides, a first side which contains an electrode configuration and a second side which contains electronic circuitry, in accordance with one or more embodiments.

FIG. 3 illustrates an implantable sensor, and electronics for driving the implantable sensor in accordance with one embodiment. FIG. 3 shows a substrate 320 having two sides, a first side 322 of which contains an electrode configuration and a second side 324 of which contains electronic circuitry (e.g., storage circuitry, processing circuitry, etc.). As may be seen in FIG. 3, a first side 322 of the substrate comprises two counter electrode-working electrode pairs 340, 342, 344, 346 on opposite sides of a reference electrode 348. A second side 324 of the substrate comprises electronic circuitry. As shown, the electronic circuitry may be enclosed in a hermetically sealed casing 326, providing a protective housing for the electronic circuitry. This allows the sensor substrate 320 to be inserted into a vascular environment or other environment which may subject the electronic circuitry to fluids. By sealing the electronic circuitry in a hermetically sealed casing 326, the electronic circuitry may operate without risk of short circuiting by the surrounding fluids. Also shown in FIG. 3 are pads 328 to which the input and output lines of the electronic circuitry may be connected. The electronic circuitry itself may be fabricated in a variety of ways. According to an embodiment, the electronic circuitry may be fabricated as an integrated circuit using techniques common in the industry.

Figure 4:
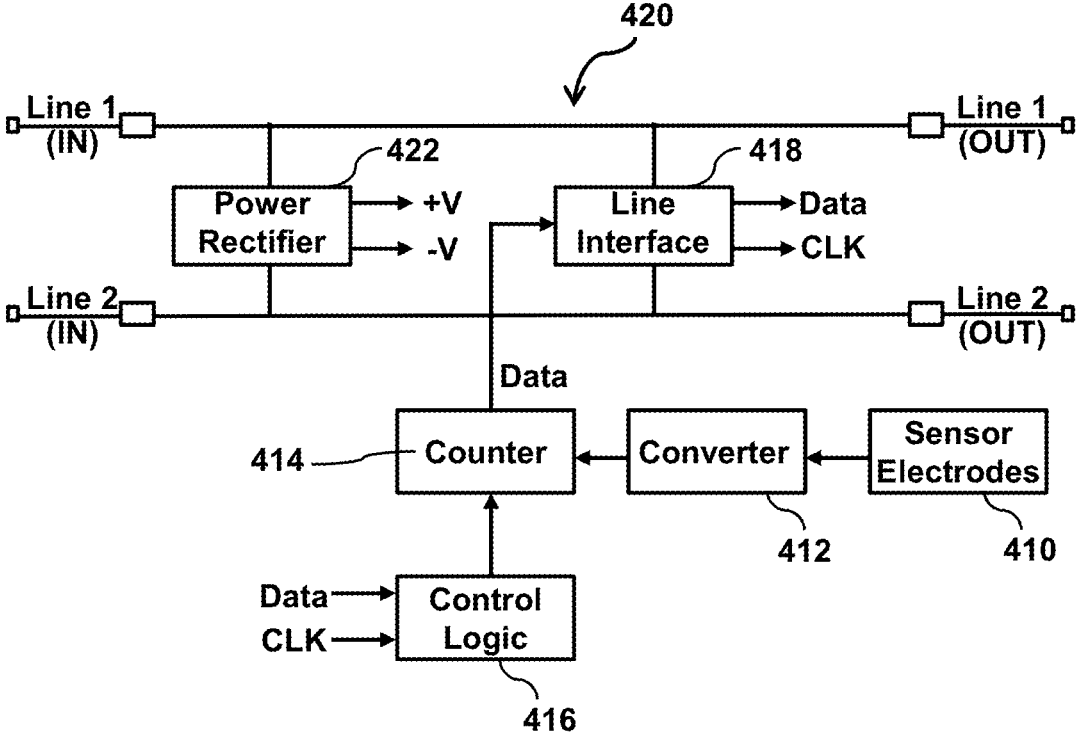
FIG. 4 illustrates a block diagram of a sensor electronics device and a sensor including a plurality of electrodes, in accordance with one or more embodiments.

FIG. 4 illustrates a general block diagram of an electronic circuit for sensing an output of a sensor according to one embodiment. At least one pair of sensor electrodes 410 may interface to a data converter 412, the output of which may interface to a counter 414. The counter 414 may be controlled by control logic 416. The output of the counter 414 may connect to a line interface 418. The line interface 418 may be connected to input and output lines 420 and may also connect to the control logic 416. The input and output lines 420 may also be connected to a power rectifier 422.

The sensor electrodes 410 may be used in a variety of sensing applications and may be configured in a variety of ways. For example, the sensor electrodes 410 may be used in physiological parameter sensing applications in which some type of biomolecule is used as a catalytic agent. For example, the sensor electrodes 410 may be used in a glucose and oxygen sensor having a GOx enzyme catalyzing a reaction with the sensor electrodes 410. The sensor electrodes 410, along with a biomolecule or some other catalytic agent, may be placed in a human body in a vascular or non-vascular environment. For example, the sensor electrodes 410 and biomolecule may be placed in a vein and be subjected to a blood stream.

Figure 5:
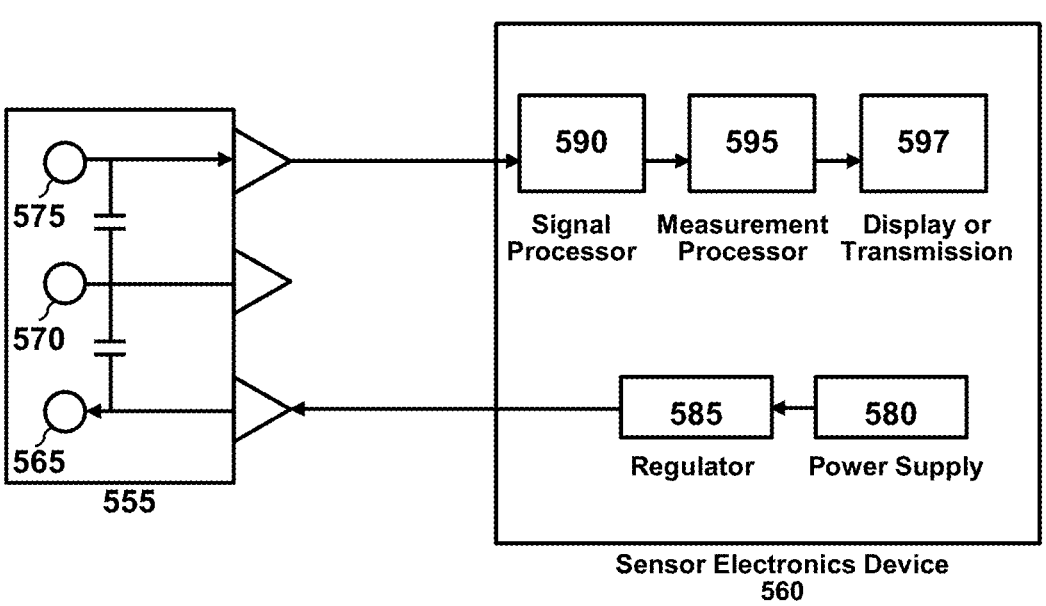
FIG. 5 illustrates an alternative embodiment of the invention including a sensor and a sensor electronics device, in accordance with one or more embodiments.
Figure 5:
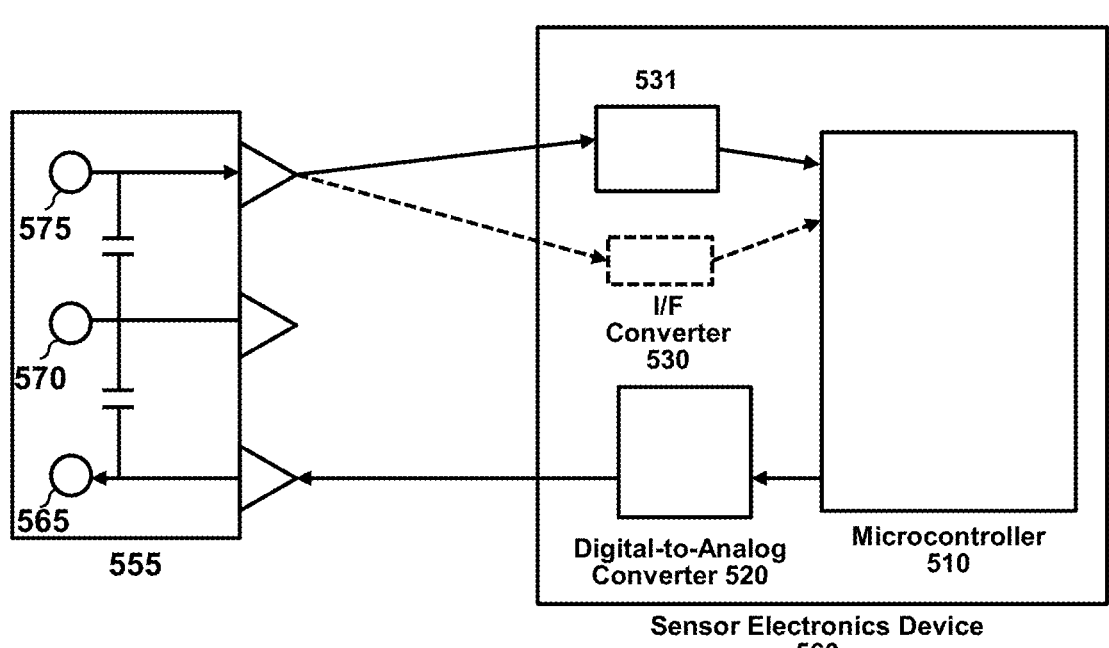

FIG. 5 illustrates a block diagram of a sensor electronics device (e.g., wearable sensor electronics devices 100 or 150, as shown in FIG. 1, or any other suitable sensor electronics device) and a sensor including a plurality of electrodes according to an embodiment herein. FIG. 5 includes system 500. System 500 includes a sensor 555 and a sensor electronics device 560. The sensor 555 includes a counter electrode 565, a reference electrode 570, and a working electrode 575. The sensor electronics device 560 includes a power supply 580, a regulator 585, a signal processor 590, a measurement processor 595, and a display/transmission module 597. The power supply 580 provides power (in the form of either a voltage, a current, or a voltage including a current) to the regulator 585. The regulator 585 transmits a regulated voltage to the sensor 555. In one embodiment, the regulator 585 transmits a voltage to the counter electrode 565 of the sensor 555.

The sensor 555 creates a sensor signal indicative of a concentration of a physiological characteristic being measured. For example, the sensor signal may be indicative of a blood glucose reading. In an embodiment utilizing subcutaneous sensors, the sensor signal may represent a level of hydrogen peroxide in a subject. In an embodiment where blood or cranial sensors are utilized, the amount of oxygen is being measured by the sensor and is represented by the sensor signal. In an embodiment utilizing implantable or long-term sensors, the sensor signal may represent a level of oxygen in the subject. The sensor signal is measured at the working electrode 575. In one embodiment, the sensor signal may be a current measured at the working electrode. In an embodiment, the sensor signal may be a voltage measured at the working electrode.

The signal processor 590 receives the sensor signal (e.g., a measured current or voltage) after the sensor signal is measured at the sensor 555 (e.g., the working electrode). The signal processor 590 processes the sensor signal and generates a processed sensor signal. The measurement processor 595 receives the processed sensor signal and calibrates the processed sensor signal utilizing reference values. In one embodiment, the reference values are stored in a reference memory and provided to the measurement processor 595. The measurement processor 595 generates sensor measurements. The sensor measurements may be stored in a measurement memory (not shown) or by circuitry (e.g., storage circuitry). The sensor measurements may be sent to a display/transmission device to be either displayed on a display in a housing with the sensor electronics or transmitted to an external device.

The sensor electronics device 560 may be a monitor which includes a display to display physiological characteristics readings. The sensor electronics device 560 may also be installed in a desktop computer, a pager, a television including communications capabilities, a laptop computer, a server, a network computer, a personal digital assistant (PDA), a portable telephone including computer functions, an infusion pump including a display (e.g., wearable sensor electronics device 100, as shown in FIG. 1), a glucose sensor including a display, and/or a combination infusion pump/glucose sensor (e.g., wearable sensor electronics device 100, as shown in FIG. 1). The sensor electronics device 560 may be housed in a blackberry (e.g., wearable sensor electronics device 150, as shown in FIG. 1), a network device, a home network device, or an appliance connected to a home network.

FIG. 5 also includes system 550. System 550 includes a sensor electronics device 560 and a sensor 555. The sensor includes a counter electrode 565, a reference electrode 570, and a working electrode 575. The sensor electronics device 560 includes a microcontroller 510 and a digital-to-analog converter (DAC) 520. The sensor electronics device 560 may also include a current-to-frequency converter (I/F converter) 530.

The microcontroller 510 includes software program code, which when executed, or programmable logic which, causes the microcontroller 510 to transmit a signal to the DAC 520, where the signal is representative of a voltage level or value that is to be applied to the sensor 555. The DAC 520 receives the signal and generates the voltage value at the level instructed by the microcontroller 510. In one embodiment, the microcontroller 510 may change the representation of the voltage level in the signal frequently or infrequently. Illustratively, the signal from the microcontroller 510 may instruct the DAC 520 to apply a first voltage value for one second and a second voltage value for two seconds.

The sensor 555 may receive the voltage level or value. In one embodiment, the counter electrode 565 may receive the output of an operational amplifier which has as inputs the reference voltage and the voltage value from the DAC 520. The application of the voltage level causes the sensor 555 to create a sensor signal indicative of a concentration of a physiological characteristic being measured. In an embodiment, the microcontroller 510 may measure the sensor signal (e.g., a current value) from the working electrode. Illustratively, a sensor signal measurement circuit 531 may measure the sensor signal. In an embodiment, the sensor signal measurement circuit 531 may include a resistor and the current may be passed through the resistor to measure the value of the sensor signal. In an embodiment, the sensor signal may be a current level signal and the sensor signal measurement circuit 531 may be a current-to-frequency (I/F) converter 530. The current-to-frequency converter 530 may measure the sensor signal in terms of a current reading, convert it to a frequency-based sensor signal, and transmit the frequency-based sensor signal to the microcontroller 510. In some embodiments, the microcontroller 510 may be able to receive frequency-based sensor signals easier than non-frequency-based sensor signals. The microcontroller 510 receives the sensor signal, whether frequency-based or non-frequency-based, and determines a value for the physiological characteristic of a subject, such as a blood glucose level. The microcontroller 510 may include program code, which when executed or run, is able to receive the sensor signal and convert the sensor signal to a physiological characteristic value. In one embodiment, the microcontroller 510 may convert the sensor signal to a blood glucose level. In an embodiment, the microcontroller 510 may utilize measurements stored within an internal memory or by circuitry (e.g., storage circuitry) in order to determine the blood glucose level of the subject. In an embodiment, the microcontroller 510 may utilize measurements stored within a memory external to the microcontroller 510 or by circuitry to assist in determining the blood glucose level of the subject.

After the physiological characteristic value is determined by the microcontroller 510, the microcontroller 510 may store measurements of the physiological characteristic values for a number of time periods. For example, a blood glucose value may be sent to the microcontroller 510 from the sensor in intervals (e.g., every second or five seconds), and the microcontroller may save sensor measurements in intervals (e.g., for five minutes or ten minutes of estimated SG values from the calibration algorithm). The microcontroller 510 may transfer the measurements of the physiological characteristic values to a display on the sensor electronics device 560 or a display interface of another user device. For example, the sensor electronics device 560 may be a monitor which includes a display that provides a blood glucose reading for a subject. In one embodiment, the microcontroller 510 may transfer the measurements of the physiological characteristic values to an output interface of the microcontroller 510. The output interface of the microcontroller 510 may transfer the measurements of the physiological characteristic values, e.g., sensor glucose values, to an external device, e.g., an infusion pump (e.g., wearable sensor electronics device 100, as shown in FIG. 1), a combined infusion pump/glucose meter (e.g., wearable sensor electronics device 100, as shown in FIG. 1), a computer, a personal digital assistant, a pager, a network appliance, a server, a cellular phone (e.g., wearable sensor electronics device 150, as shown in FIG. 1), or any computing device.

Figure 6:
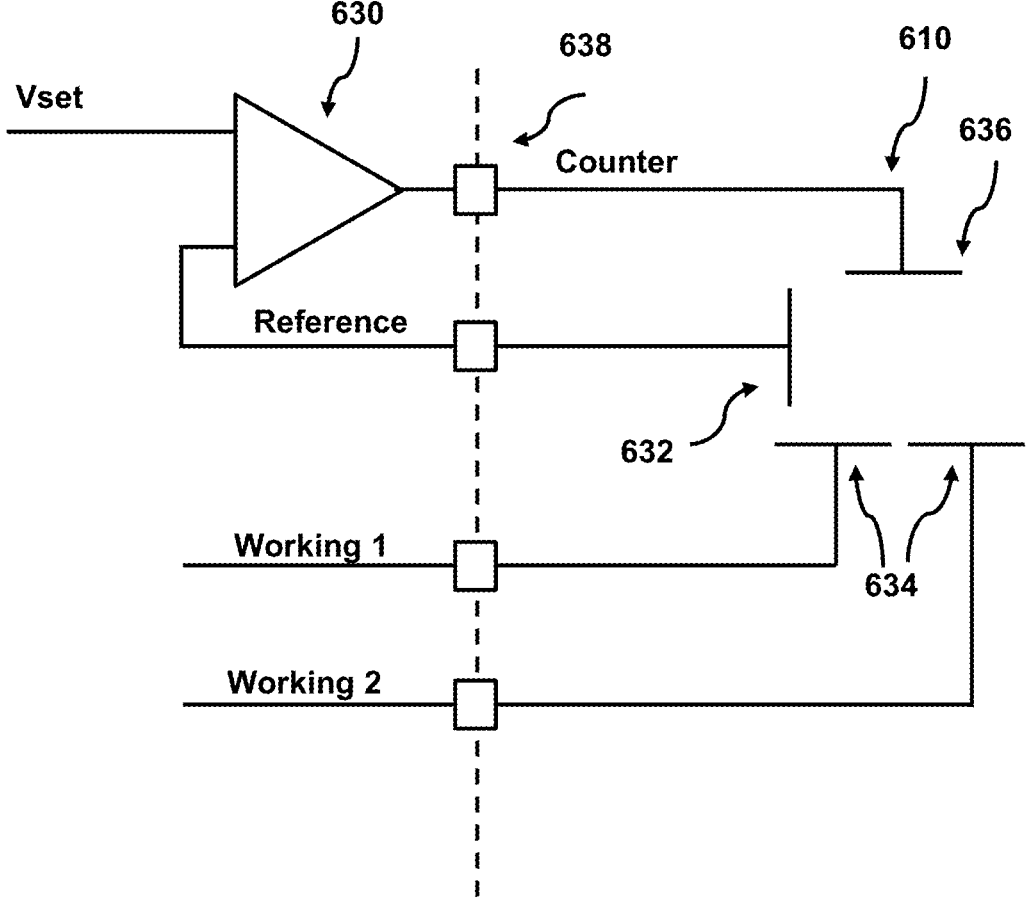
FIG. 6 illustrates an electronic block diagram of the sensor electrodes and a voltage being applied to the sensor electrodes, in accordance with one or more embodiments.

FIG. 6 illustrates an electronic block diagram of the sensor electrodes and a voltage being applied to the sensor electrodes according to an embodiment. In some embodiments, FIG. 6 may illustrate an electrode with a GOx sensor and/or an electrode capable of sensing GOx. For example, FIG. 6 may illustrate a working electrode with a GOx sensor that functions with a background electrode in which the background electrode has no GOx sensor (e.g., as discussed below in relation to FIGS. 8 and 9). The system may then compare the first signal and the second signal to detect ingestion of a medication by the user. The system may generate a sensor glucose value based on the comparison. In the embodiment illustrated in FIG. 6, an op amp 630 or other servo-controlled device may connect to sensor electrodes 610 through a circuit/electrode interface 638. The op amp 630, utilizing feedback through the sensor electrodes, attempts to maintain a prescribed voltage (what the DAC may desire the applied voltage to be) between a reference electrode 632 and a working electrode 634 by adjusting the voltage at a counter electrode 636. Current may then flow from a counter electrode 636 to a working electrode 634. Such current may be measured to ascertain the electrochemical reaction between the sensor electrodes 610 and the biomolecule of a sensor that has been placed in the vicinity of the sensor electrodes 610 and used as a catalyzing agent. The circuitry (e.g., processing circuitry) disclosed in FIG. 6 may be utilized in a long-term or implantable sensor or may be utilized in a short-term or subcutaneous sensor.

In a long-term sensor embodiment, where a GOx enzyme is used as a catalytic agent in a sensor, current may flow from the counter electrode 636 to a working electrode 634 only if there is oxygen in the vicinity of the enzyme and the sensor electrodes 610. Illustratively, if the voltage set at the reference electrode 632 is maintained at about 0.5 volts, the amount of current flowing from the counter electrode 636 to a working electrode 634 has a fairly linear relationship with unity slope to the amount of oxygen present in the area surrounding the enzyme and the electrodes. Thus, increased accuracy in determining an amount of oxygen in the blood may be achieved by maintaining the reference electrode 632 at about 0.5 volts and utilizing this region of the current-voltage curve for varying levels of blood oxygen. Different embodiments may utilize different sensors having biomolecules other than a glucose oxidase enzyme and may, therefore, have voltages other than 0.5 volts set at the reference electrode.

As discussed above, during initial implantation or insertion of the sensor 610, the sensor 610 may provide inaccurate readings due to the adjusting of the subject to the sensor and also electrochemical byproducts caused by the catalyst utilized in the sensor. A stabilization period is needed for many sensors in order for the sensor 610 to provide accurate readings of the physiological parameter of the subject. During the stabilization period, the sensor 610 does not provide accurate blood glucose measurements. Users and manufacturers of the sensors may desire to improve the stabilization timeframe for the sensor so that the sensors can be utilized quickly after insertion into the subject's body or a subcutaneous layer of the subject.

In previous sensor electrode systems, the stabilization period or timeframe was one hour to three hours. In order to decrease the stabilization period or timeframe and increase the timeliness of accuracy of the sensor, a sensor (or electrodes of a sensor) may be subjected to a number of pulses rather than the application of one pulse followed by the application of another voltage. for the second time period. In one embodiment, the first voltage may be 1.07 volts. In an embodiment, the first voltage may be 0.535 volts. In an embodiment, the first voltage may be approximately 0.7 volts.

Figure 7:
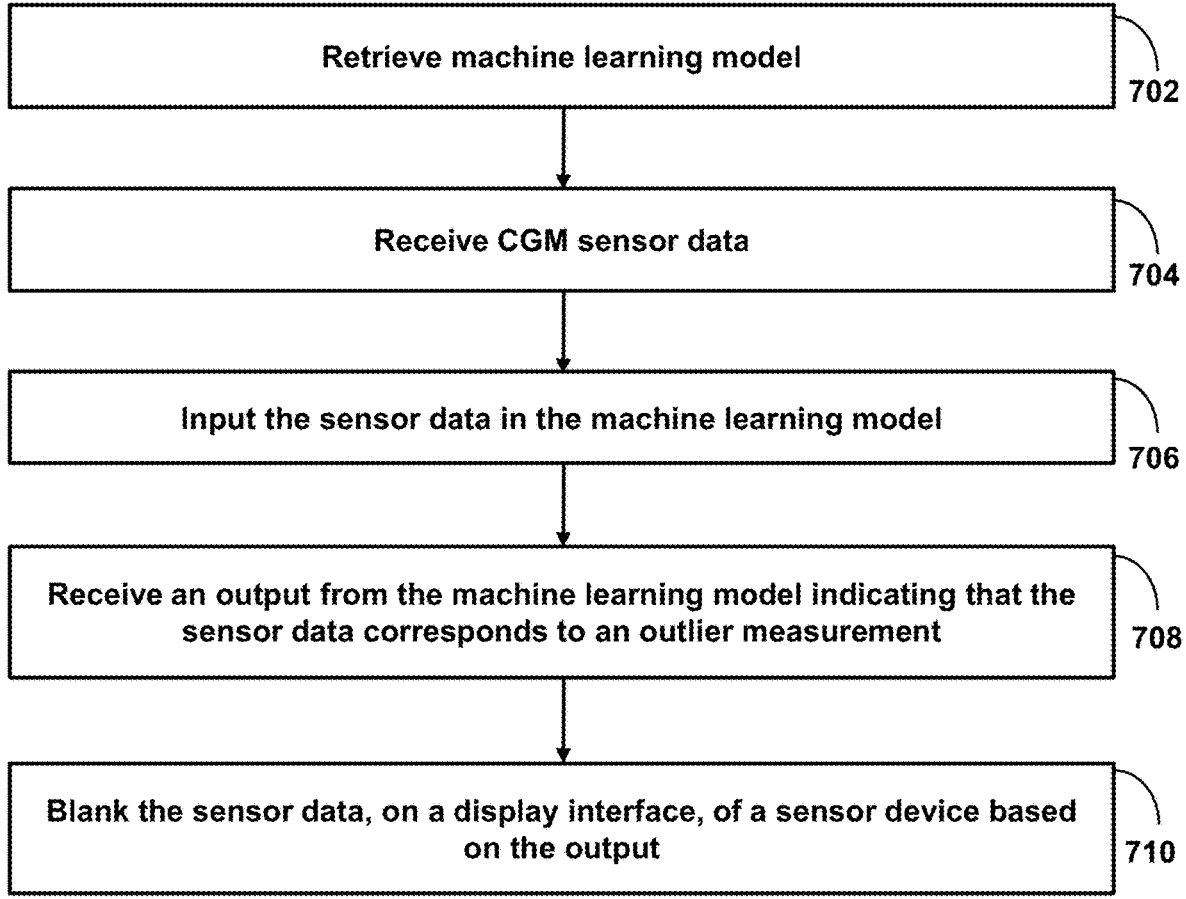
FIG. 7 shows a flowchart of the steps involved in applying machine learning models to improve integrated continuous glucose monitoring ("iCGM") performance of continuous glucose monitoring ("CGM") calibration algorithms, in accordance with one or more embodiments.

FIG. 7 shows a flowchart of the steps involved in applying machine learning models (e.g., supervised machine learning models, unsupervised machine learning models, semi-supervised machine learning models, or any other suitable type of machine learning model) to improve integrated continuous glucose monitoring ("iCGM") performance of continuous glucose monitoring ("CGM") calibration algorithms by classifying outlier measurements based on iCGM criteria, in accordance with one or more embodiments. For example, process 700 may represent the steps taken by one or more devices as shown in FIGS. 1-6.

At step 702, process 700 (e.g., using components described in FIGS. 1-6) retrieves a machine learning model. In some embodiments, the machine learning model is trained to identify outlier measurements based on iCGM criteria using training data. For example, the training data may comprise clinical data on iCGM performance. As discussed below in relation to FIG. 7, process 700 may classify the training data in a number of ways. For example, in some embodiments, process 700 may determine whether a set of training sensor data in the training data corresponds to known classification, wherein the known classification comprises a large negative bias, large positive bias, or nominal accuracy. In some embodiments, in order to determine whether the training sensor data has a large negative bias, large positive bias, or nominal accuracy, process 700 may compare the training sensor data to one or more thresholds (e.g., a negative bias threshold or a positive bias threshold). In some embodiments, this determination may be calibration algorithm dependent since the bias is calculated from the sensor glucose value. Based on whether the training sensor data satisfies the negative bias threshold, process 700 may determine whether the training sensor data has outlier performance. Based on whether the training sensor data satisfies the positive bias threshold, process 700 may determine whether the training sensor data has a large positive bias. If the training sensor data does not satisfy either threshold, process 700 may determine that the training sensor data has nominal accuracy. It should be noted that iCGM criteria are calculated on aggregate data. While it may be possible to calculate bias based on the estimated SG values (e.g., predicted from the sensor data), the machine learning model can predict signals that have outlier behavior that can skew iCGM performance downstream (e.g., as calculated based on the aggregate data).

In some other embodiments, process 700 may determine whether a set of training sensor data in the training data corresponds to known classification, wherein the known classification comprises poor accuracy, intermediate accuracy, or good accuracy. In some embodiments, accuracy may be measured using the mean absolute relative difference (MARD) and bias. Depending on the range of the estimated SG value, a hit criteria for iCGM may shift between the MARD and bias metrics. For example, for certain SG values, the hit criteria may specify a certain bias, while for other SG values, the hit criteria may specify a MARD. In some embodiments, in order to determine whether the training sensor data has poor accuracy, intermediate accuracy, or good accuracy, process 700 may compare the training sensor data to one or more thresholds (e.g., an intermediate accuracy threshold and a good accuracy threshold). Based on whether the training sensor data satisfies the intermediate accuracy threshold, process 700 may determine whether the training sensor data has intermediate accuracy. Based on whether the training sensor data satisfies the good accuracy threshold, process 700 may determine whether the training sensor data has good accuracy. If the training sensor data does not satisfy either threshold, process 700 may determine that the training sensor data has poor accuracy. In some embodiments, process 700 may label the training sensor data with the known classification.

At step 704, process 700 (e.g., using components described in FIGS. 1-6) receives CGM sensor data. For example, process 700 may receive the sensor data at the sensor device. For example, the sensor data may comprise an Interstitial Current Signal ("Isig"), counter voltage ("Vcntr"), and Electrochemical Impedance Spectroscopy Signal ("EIS"). In some embodiments, process 700 may receive the sensor data in first time intervals (e.g., every five minutes or any other predetermined period of time).

At step 706, process 700 (e.g., using components described in FIGS. 1-6) inputs the sensor data in the machine learning model. For example, inputting the sensor data in the machine learning model may comprise generating a multi-dimensional feature input based on the sensor data. In some embodiments, the multi-dimensional feature input may include Isig, Isig rate of change, Isig Noise, real and imaginary EIS signals at a range of frequencies, sensor age (e.g., time since initialization), Vcntr, or other features.

At step 708, process 700 (e.g., using components described in FIGS. 1-6) receives an output from the machine learning model indicating that the sensor data corresponds to an outlier measurement. In some embodiments, the machine learning model may indicate a known classification to which the sensor data corresponds (e.g., large negative bias, large positive bias, nominal accuracy, poor accuracy, intermediate accuracy, good accuracy, etc.).

At step 710, process 700 (e.g., using components described in FIGS. 1-6) blanks the sensor data based on the output. For example, blanking may comprise temporarily removing, blocking, replacing, freezing, or otherwise blanking the sensor data (e.g., eschew transmitting sensor data to another device, eschew displaying sensor data on a display interface). In some embodiments, blanking outlier signals may limit the number of poor sensor glucose estimates that reach the user, which could lead to adverse treatment decisions. For example, reporting a sensor glucose value that is over-reading when a user is in a hypoglycemic state could lead to incorrect treatment decisions, such as insulin dosing that further drives the user deeper into hypoglycemia. Blanking outliers can reduce the instances in which sensor performance falls into the high-risk zones of the Clarke Error Grid (e.g., which quantifies clinical accuracy of patient estimates of their current blood glucose as compared to the blood glucose value obtained in their meter) and can improve accuracy and ability to meet iCGM. In some embodiments, to blank the sensor data, process 700 (e.g., processors) may determine a variable for a CGM calibration algorithm based on the output from the machine learning model and determine whether to blank the sensor based on the CGM calibration algorithm output.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-5 could be used to perform one or more of the steps in FIG. 7.

FIG. 8 shows a flowchart of the steps involved in applying machine learning models to detect and correct for erroneous sensor use conditions, in accordance with one or more embodiments. For example, process 800 may represent the steps taken by one or more devices as shown in FIGS. 1-6.

At step 802, process 800 (e.g., using components described in FIGS. 1-6) retrieves a machine learning model that is trained to identify erroneous sensor use conditions based on sensor data error patterns. For example, error patterns may be characteristics (e.g., behaviors, trends, patterns) of the sensor data. For example, in some embodiments, these characteristics of the sensor data may include a downward trend over time (e.g., over the lifetime of a sensor), a spike or drop-off in a signal followed by a return to normal in a short time (e.g., over several seconds), an abnormality that repeats several times over a time period (e.g., several minutes), or other behaviors, trends, or patterns. In some embodiments, the error pattern may depend on a time frame within which it occurs. For example, a certain behavior of a signal may only be characterized as an error pattern if it occurs within a certain time period (e.g., five seconds). In some embodiments, a certain behavior of a signal may only be characterized as an error pattern if it reaches a threshold magnitude (e.g., a minimum required deviation from a normal signal). In some embodiments, a behavior of a signal may only be characterized as an error pattern if it reaches a certain number of repetitions (e.g., three repetitions). Other data characteristics may factor into error pattern detection. In some embodiments, the machine learning model may be trained to recognize error patterns (e.g., such as those described above) using training data. For example, the training data may comprise clinical data on erroneous sensor use conditions. In some embodiments, the training data may additionally include context information (e.g., historic information, sensor data features, etc.) relating to the sensor data. In such cases, sensor data error patterns featuring a known erroneous sensor use condition may be labeled and used to train the system to identify the sensor data error patterns in non-training scenarios. In some embodiments, the system may retrieve a machine learning model that is trained for a particular user based on clinical data from similar users. For example, the system may use clinical data from users of a similar age, height, weight, or level of athleticism, such that the machine learning model is trained to recognized error patterns that are most likely to occur for the user.

At step 804, process 800 (e.g., using components described in FIGS. 1-6) receives CGM sensor data. For example, process 800 may receive the CGM sensor data at a sensor device. For example, the sensor device may be associated with a user device of a user. The sensor data may be real-time sensor data from the sensor device. At step 806, process 800 (e.g., using circuitry described in FIGS. 1-6) inputs the sensor data into the machine learning model.

At step 808, process 800 (e.g., using components described in FIGS. 1-6) receives an output from the machine learning model indicating an erroneous sensor use condition. For example, the erroneous sensor use condition may be based on an error pattern identified in the sensor data. In some embodiments, the erroneous sensor use condition may be further based upon the context information relating to the sensor data. In some embodiments, identified error patterns may be associated with multiple erroneous sensor use conditions.

It is contemplated that the steps or descriptions of FIG. 8 may be used with any other embodiment of this disclosure. In addition, the steps and descriptions described in relation to FIG. 8 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-5 could be used to perform one or more of the steps in FIG. 8.

FIG. 9 shows a machine learning model system for making predictions that facilitate both classification of outlier measurements based on iCGM criteria and detection and correction of erroneous sensor use conditions, in accordance with one or more embodiments.

In some embodiments, the machine learning model system may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

In some embodiments, the machine learning model system may update its configurations (e.g., weights, biases, or other parameters) based on its assessment of the predictions. Memory may store training data and one or more trained machine learning models.

As an example, a machine learning model 900 may take inputs 902 and provide outputs 904. In one use case, outputs 904 may be fed back (e.g., active feedback) to machine learning model 900 as input to train machine learning model 900 (e.g., alone or in conjunction with user indications of the accuracy of outputs 904, labels associated with the inputs 902, or with other reference feedback information). In another use case, machine learning model 900 may update its configurations (e.g., weights, biases, or other parameters) based on its assessment of its prediction (e.g., outputs 904) and reference feedback information (e.g., user indication of accuracy, reference labels, or other information). In another use case, where machine learning model 900 is a neural network, connection weights may be adjusted to reconcile differences between the neural network's prediction and the reference feedback. In a further use case, one or more neurons (or nodes) of the neural network may require that their respective errors be sent backward through the neural network to them to facilitate the update process (e.g., backpropagation of error). Updates to the connection weights may, for example, be reflective of the magnitude of error propagated backward after a forward pass has been completed. In this way, for example, the machine learning model 900 may be trained to generate better predictions.

For example, in some embodiments, inputs 902 may comprise CGM sensor data (e.g., sensor glucose data), and reference feedback information 904 (which feeds back as input to the machine learning model 900) may include clinical data on iCGM performance. For example, the clinical data may be labeled training data (e.g., labeled as outlier, not outlier). Accordingly, when machine learning model 900 receives a particular glucose measurement as input 902, machine learning model 900 may provide an output 904 including a prediction of whether the measurement is an outlier. This outlier information may be used to correct future signals.

In some embodiments, the system may label the clinical data according to known classifications. In some embodiments, the known classifications may be based upon the FDA iCGM special requirements (e.g., the known classifications may be defined such that the outputs 904 conform to the FDA iCGM special requirements). For example, known classifications may include large negative bias, large positive bias, nominal accuracy, or other labels with respect to the iCGM criteria. For example, a large negative bias may indicate that a particular measurement is underestimated, undervalued, or otherwise too low. A large positive bias may indicate that a particular measurement is overestimated, overvalued, or otherwise too high. In some embodiments, these known classifications may describe the CGM sensor data relative to an average measurement or range across the sensor data, an average measurement or range for sensor data associated with a user of the sensor device, or another reference. In some embodiments, the system may take calibration measurements periodically (e.g., every 4-6 hours or any other predetermined period of time) and derive a reference value from the calibration measurements. The system may thus determine positive and negative bias relative to the reference value. Finally, when machine learning model 900 receives a particular glucose measurement as input 902 to, machine learning model 900 may provide an output 904 including a prediction of whether the measurement corresponds to a large negative bias, large positive bias, or nominal accuracy.

In some embodiments, known classifications may include poor accuracy, intermediate accuracy, good accuracy, or other labels. For example, accuracy labels may correspond to wear times, consistency or inconsistency of readings (e.g., as compared to data for a particular user, training data as a whole, etc.), or other indicators of accuracy. In some embodiments, as described above, the system may take calibration measurements periodically (e.g., every 4-6 hours or any other predetermined period of time) and derive a reference value from the calibration measurements. The system may determine accuracy levels relative to the reference value. Accordingly, when machine learning model 900 receives a particular glucose measurement as input 902 to, machine learning model 900 may provide an output 904 including a prediction of whether the measurement corresponds to a poor accuracy, intermediate accuracy, or good accuracy.

In some embodiments, machine learning model 900 may receive a multi-dimensional feature input based on the sensor data. For example, the inputs 902 received by machine learning model 900 may comprise features such as an EIS feature, Isig trending feature, Isig rate of change feature, previous Isig, previous Vcntr, or other feature inputs. Further description of the above feature inputs can be found in U.S. patent Ser. No. 16/773,422, entitled METHODS, SYSTEMS, AND DEVICES FOR CONTINUOUS GLUCOSE MONITORING, which is herein incorporated by reference in its entirety. In some embodiments, the outputs 904 of machine learning model 900 may depend on combinations of the above feature inputs. For example, certain combinations of Isig, EIS, and Vcntr feature inputs may cause machine learning model 900 to classify the signals as outliers (e.g., or large negative bias, large positive bias, poor accuracy, etc.). In some embodiments, other combinations of Isig, EIS, and Vcntr feature inputs may cause machine learning model 900 to classify the signals as not outliers (e.g., or nominal accuracy, intermediate accuracy, good accuracy, etc.). In some embodiments, the machine learning model may use hit criteria (e.g., as described above) to classify the multi-dimensional feature input as an outlier or not an outlier.

In some embodiments, inputs 902 may comprise sensor data from a sensor device and reference feedback information 904 (which is fed back as input to the machine learning model 900) may include clinical data on erroneous sensor use conditions. For example, the clinical data may be labeled training data, which may include a library of error patterns. In some embodiments, the error patterns may be labeled with corresponding erroneous sensor use conditions. For example, erroneous sensor use conditions may include sensitivity loss, loss of signal, signal spiking, environmental errors (e.g., moisture, heat), or other conditions. Accordingly, when a particular glucose measurement is provided as input 902 to machine learning model 900, machine learning model 900 may provide an output 904 including a prediction of an erroneous sensor use condition based on a detected error pattern.

In some embodiments, inputs 902 may further comprise context information relating to the sensor data. In some embodiments, context information may include pattern definition. For example, error patterns may include combinations of patterns of various sensor input features. In this example, context information may include information about the various components (e.g., sensor input features) of the sensor data and how the error pattern affects these components. In some embodiments, the context information may include historic information relating to the sensor data over a time period. For example, such historic information may include information about behaviors, trends, or patterns of the sensor data over a certain time period leading up to a detected error pattern. In some embodiments, behaviors, trends, or patterns of the sensor data may include downward trends, noisy conditions, a history of error patterns, or other context information. In some embodiments, the time period may be several seconds, minutes, hours, or days, or the time period may be the lifetime of the sensor device. The context information may be important for distinguishing between identical error patterns with different underlying erroneous sensor use conditions. For example, for an error pattern (e.g., low signal) within a first context (e.g., stable history), the system may determine that a first erroneous sensor use condition (e.g., temporary signal loss) is associated with the error pattern. In another example, for the same error pattern (e.g., low signal) within a second context (e.g., downward trend), the system may determine that a second erroneous sensor use condition (e.g., sensitivity loss) is associated with the error pattern. The context information is thus vital to determining the correct erroneous sensor use condition associated with a given error pattern and the correct resolution for correcting the erroneous sensor use condition. In this example, output 904 may be further based upon the context information relating to the sensor data.

In some embodiments, inputs 902 may comprise sensor data from a sensor device and reference feedback information 904 (which is fed back as input to the machine learning model 900) may include data on resolutions associated with various erroneous sensor use conditions. For example, the system may use retrospective techniques to apply resolutions to the training data. The system may determine which resolutions are most effective for resolving each erroneous sensor use condition. Thus, the training data may be labeled training data (e.g., error patterns or erroneous sensor use conditions labeled with effective resolutions). Accordingly, when particular sensor data is provided as input 902 to machine learning model 900, machine learning model 900 may provide an output 904 including a prediction of a resolution that is likely to correct for a detected erroneous sensor use condition.

While machine learning model 900 is described in relation to the foregoing examples, it should be understood that the system may train machine learning model 900 to classify or predict characteristics or errors of sensor data according to any other criteria or based on any other inputs. In some embodiments, the system may utilize outputs from machine learning model 900 to determine blanking and termination of signals (e.g., as described below in relation to FIGS. 10 and 11) or to determine resolutions for erroneous sensor use conditions (e.g., as described below in relation to FIGS. 10 and 12).

FIG. 10 shows a flow diagram 1000, in accordance with one or more embodiments. As shown schematically in FIG. 10, the methods and systems described herein include: a sensor feature generator 1002, a blood glucose calibrator 1004, a sensor glucose modeler 1006, a conditional blanker and terminator 1008, and an error detector and corrector 1010. In some embodiments, input data (i.e., interstitially measured current (Isig), counter voltage (Vcntr), electrochemical impedance spectroscopy (EIS), and blood glucose calibration values (BG)) may pass through the algorithm to be transformed to sensor glucose values, or SG. The Table below shows the information input and output from each of the four components.

Description of the Information Transfer

| Information Content | Component 1002 | Component 1004 | Component 1006 | Component 1008 | Component 1010 |
|---|---|---|---|---|---|
| Input signals, Isig, Vcntr, EIS, BG | Input | N/A | N/A | Input | N/A |
| Base and Derivative Sensor Features Requiring No Calibration | Output | Input | Input | Input | Input |
| Base and Derivative Sensor Features Requiring BG Calibration | N/A | Output | Input | Input | Input |
| Initial Estimates of Sensor Glucose Values | N/A | N/A | Output | Input | Output |
| Final Estimates of Sensor Glucose Values | N/A | N/A | N/A | Output | N/A |

In some embodiments, the input data may flow through components 1002, 1004, 1006, and 1008 (i.e., bypassing component 1010). For example, components 1002, 1004, and 1006 may complete sensor feature generation, BG calibration, and SG modelling, respectively, and component 1008 may classify the sensor data and blank or terminate signals accordingly. In some embodiments, conditional blanker and terminator 1008 may include or be associated with machine learning model 900, as shown in FIG. 9. For example, machine learning model 900 may classify CGM sensor data. For example, machine learning model 900 may classify the sensor data as outlier/not outlier, as having large negative bias/large positive bias/nominal accuracy, or as having poor accuracy/intermediate accuracy/good accuracy. In some embodiments, conditional blanker and terminator 1008 may blank the sensor data (e.g., eschew transmitting sensor data to another device, eschew displaying sensor data on a display interface) based on the output from machine learning model 900. For example, if the output from machine learning model 900 indicates that a measurement from the sensor data is not an outlier (e.g., does not breach a threshold), conditional blanker and terminator 1008 may not blank that measurement. Similarly, if the output from machine learning model 900 indicates that a measurement has intermediate, normal, or good accuracy, conditional blanker and terminator 1008 may not blank that particular measurement. In some embodiments, if the output from machine learning model 900 indicates that a measurement from the sensor data is an outlier, conditional blanker and terminator 1008 may blank that measurement. Similarly, if the output from machine learning model 900 indicates that a measurement has a large bias (e.g., positive or negative) or has poor accuracy, conditional blanker and terminator 1008 may blank that measurement. In some embodiments, conditional blanker and terminator 1008 may blank certain measurements based on any other classifications output by machine learning model 900.

In some embodiments, blanking the CGM sensor data (e.g., via a display interface) may include determining a variable for the CGM calibration algorithm based on the output from machine learning model 900 (e.g., as shown in FIG. 7). In some embodiments, the variable for the CGM calibration algorithm may depend on whether machine learning model 900 outputs an outlier classification (e.g., nominal accuracy, intermediate accuracy, good accuracy, etc.) or a non-outlier classification (e.g., large positive bias, large negative bias, poor accuracy, etc.). In some embodiments, conditional blanker and terminator 1008 may determine whether to blank the sensor data based on the output from the CGM calibration algorithm.

In some embodiments, conditional blanker and terminator 1008 may additionally or alternatively terminate a sensor (e.g., stop transmitting any sensor data from that sensor and/or stop displaying any sensor data from that sensor). For example, conditional blanker and terminator 1008 may monitor measurements that have been blanked (i.e., outliers). Conditional blanker and terminator 1008 may track a number of consecutive blanked measurements (e.g., within a certain time frame). For example, conditional blanker and terminator 1008 may use an outlier counter to track blanked measurements and determine when to terminate a sensor. In some embodiments, when machine learning model 900 classifies a measurement as not an outlier, the system may reset the outlier counter (e.g., to zero). In some embodiments, when machine learning model 900 classifies a certain number of measurements in a row as not outliers, the system may reset the outlier counter. For example, machine learning model 900 classifies five measurements as not outliers, the system may reset the outlier counter. In some embodiments, the system may reset the outlier counter based on measurements that machine learning model 900 classifies as having nominal accuracy, intermediate accuracy, good accuracy, etc.

If conditional blanker and terminator 1008 identifies a measurement that has been classified as an outlier (e.g., or large positive bias, large negative bias, poor accuracy, etc.) by machine learning model 900, the system may increase the outlier counter. For example, the system may increment the outlier counter by one. In this example, the outlier counter may continue to increase when outlier measurements are received. As described above, the system may reset the outlier counter at any time in response to receiving one or more measurements classified as non-outliers. The outlier counter may continue to increase in response to outlier measurements until a threshold is breached. For example, the threshold may be predetermined. In some embodiments, the threshold may dynamically change based on wear time, battery life, or other factors. In some embodiments, the threshold may have an associated time limit. For example, in some embodiments, the outlier counter must breach the threshold within a certain time frame (e.g., 1 hour) in order to terminate the signal (e.g., stop transmitting any sensor data from that sensor and/or stop displaying any sensor data from that sensor). In some embodiments, once the system terminates the signal, conditional blanker and terminator 1008 may alert the user that the sensor must be replaced (e.g., via a display interface).

FIG. 11 shows the schematic 1100 of the sensor feature generator 1002 of FIG. 10, in accordance with one or more embodiments. As shown, the consumes the following input signals: Isig (e.g., 1-minute) 1102, Vcntr (e.g., 5-minute) 1104, and EIS (e.g., 15-30 minutes) 1106. The Isig signals are collected over 5 minutes to generate a 5-minute Isig signal 1108 and the EIS signal is validated at 1112. The latter two signals are then used, along with preprocessing, to generate 5-minute and derivative features (e.g., 1110, 1116). In some embodiments, measurement frequency of signals can change depending on the hardware design, e.g., Vcntr may be measured at 1-minute and EIS may be measured more frequently, depending on battery life and memory size limitations. The Table below provides a description of the input signals to sensor feature generator 1002. Sensor feature generator 1002 will make these input signals, as well as the signals it generates, available to blood glucose calibrator 1004, sensor glucose modeler 1006, and conditional blanker and terminator 1008 (e.g., at 1114).

Description of the Input Signals to Sensor Feature Generator 1002

| Signal | Description | Input Time Lapse | Output Time Lapse |
|---|---|---|---|
| Isig | Interstitial Current Signal | 1 minute | 5 minutes |
| Vcntr | Counter Voltage Signal | 5 minutes | 5 minutes |

-continued

| Signal | Description | Input Time Lapse | Output Time Lapse |
|---|---|---|---|
| EIS | Electrochemical Impedance Spectroscopy Signal | 15 to 30 minutes | 5 minutes |

As shown in FIG. 11, the system may process the Isig, Vcntr, and EIS signals based on the first time interval (e.g., 5-minute features 1110). In some embodiments, the packet, including all or some of these signals, may be used to generate a calibrated SG value, which is displayed to the user (e.g., via a display interface). At any point in each interval, the system may blank the output values provided to the user (e.g., as described above in relation to FIG. 10) in response to the system classifying a signal included in the interval as an outlier. In some embodiments, the outlier counter described above may utilize the first interval to reset or increase. In other words, the system may reset the outlier counter or increase the outlier counter based identifying a measurement included in the interval as an outlier. An aggregation of packets including blanked signals (e.g., multiple consecutive five-minute increments) may cause the system to terminate the sensor (e.g., stop transmitting any sensor data from that sensor and/or stop displaying any sensor data from that sensor).

Returning to FIG. 10, error detector and corrector 1010 may function in parallel with sensor glucose modeler 1006. For example, error detector and corrector 1010 may take the same inputs as sensor glucose modeler 1006 (e.g., as shown in the Table above). In some embodiments, outputs from error detector and corrector 1010 may, at times, feed into conditional blanker and terminator 1008. For example, if error detector and corrector 1010 detects no error patterns in the sensor data, the output from sensor glucose modeler 1006 may function as the initial estimates of sensor glucose values, as input into conditional blanker and terminator 1008. If error detector and corrector 1010 detects an error pattern in the sensor data, the system may switch over such that the output from error detector and corrector 1010 functions as the initial estimates of sensor glucose values, as input into conditional blanker and terminator 1008. Thus, while sensor glucose modeler 1006 and error detector and corrector 1010 may process the sensor data in parallel, the output from sensor glucose modeler 1006 may be the primary input into conditional blanker and terminator 1008 under circumstances in which no error patterns are detected in the sensor data and the output from error detector and corrector 1010 may be the primary input into conditional blanker and terminator 1008 under circumstances in which one or more error patterns are detected in the sensor data. In other words, if error detector and corrector 1010 detects no error patterns in the signal, flow diagram 1000 may function as if it were independent of error detector and corrector 1010.

In some embodiments, error detector and corrector 1010 may identify a resolution in response to a detected erroneous sensor use condition. For example, error detector and corrector 1010 may identify a resolution that is associated with the detected erroneous sensor use condition. In some embodiments, the resolution may be associated with the detected erroneous sensor use condition via a database, library of patterns, library of resolutions, or by some other means. In some embodiments, the resolution may be associated with the detected erroneous sensor use condition via an output from a machine learning model (e.g., machine learning model 900), as discussed above in relation to FIG. 9. In some embodiments, error detector and corrector 1010 may implement the identified resolution or may cause the identified resolution to be implemented (e.g., by another component). In some embodiments, the system may implement the identified resolution by manipulating the sensor glucose data that is displayed on a user device (e.g., via a display interface). For example, the system (e.g., conditional blanker and terminator 1008) may blank the sensor glucose data from the sensor device. In another example, the system may flag a user of the sensor device (e.g., by generating an alert, informing the user of the erroneous sensor use condition, requesting an action from a user, etc.). In some embodiments, the system (e.g., error detector and corrector 1010) may implement the identified resolution by manipulating (e.g., processing) the sensor data directly. For example, error detector and corrector 1010 may adjust a signal, add a filter to a signal, adjust a filter of a signal, replace a signal (e.g., with a trending signal, a signal from a library, etc.), or otherwise manipulate or process the sensor data.

In some embodiments, error detector and corrector 1010 may include or be associated with machine learning model 900, as shown in FIG. 9. For example, machine learning model 900 may detect error patterns in the sensor data or identify a resolution in response to a detected erroneous sensor use condition. In some embodiments, machine learning model 900 may generate additional predictions which error detector and corrector 1010 may utilize for identifying and correcting erroneous sensor use conditions.

FIG. 12 shows a graph 1200 highlighting error patterns in sensor data, in accordance with one or more embodiments. As shown in graph 1200, the system (e.g., error detector and corrector 1010, as shown in FIG. 10) may identify various error patterns, such as error pattern 1202 and error pattern 1204. Both error pattern 1202 and error pattern 1204 may demonstrate a dropping off of a signal. In this example, error detector and corrector 1010 may identify an underlying erroneous sensor use condition for each error pattern based on the error pattern, context information of the sensor data (e.g., as described above), or other information relating to the sensor data.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

1. A method comprising: receiving, at a sensor device, CGM sensor data; inputting, at the sensor device, the sensor data in a machine learning model, wherein the machine learning model is trained to identify outlier measurements based on sensor glucose-dependent performance against iCGM criteria using training data comprising clinical data on iCGM performance; receiving, at the sensor device, an output from the machine learning model indicating that the sensor data corresponds to an outlier measurement of the outlier measurements; and blanking the sensor data based on the output.

2. The method of embodiment 1, wherein the machine learning model is trained using a set of training sensor data that is labeled according to known classifications, the known classifications comprising a large negative bias, large positive bias, or nominal accuracy.

3. The method of any of embodiments 1-2, wherein the machine learning model is trained using a set of training sensor data that is labeled according to known classifications, the known classifications comprising poor accuracy, intermediate accuracy, or good accuracy.

4. The method of any of embodiments 1-3, wherein the sensor data comprises a current signal, a voltage signal, or impedance spectroscopy signals.

5. The method of embodiment 4, wherein inputting the sensor data in the machine learning model comprises generating a multi-dimensional feature input based on the sensor data.

6. The method of any of embodiments 1-5, wherein blanking the sensor data based on the output further comprises: determining a variable for a CGM calibration algorithm based on the output; and determining whether to blank the sensor data based on the output from the from the machine learning model.

7. The method of any of embodiments 1-6, wherein the sensor data is received in first time intervals.

8. The method of any of embodiments 1-7, further comprising: resetting an outlier counter based on determining that a first sensor datapoint does not correspond to an outlier measurement; causing the outlier counter to be increased based on determining that a second sensor datapoint corresponds to an outlier measurement; comparing the outlier counter to a threshold; and terminating the sensor device based on determining that the outlier counter has breached the threshold.

9. A method comprising: receiving, at a sensor device, CGM sensor data; inputting, at the sensor device the sensor data into a machine learning model, wherein the machine learning model is trained to identify erroneous sensor use conditions based sensor data error patterns using training data comprising clinical data on erroneous sensor use conditions; and receiving, at the sensor device, an output from the machine learning model indicating an erroneous sensor use condition based on an error pattern identified in the sensor data.

10. The method of embodiment 9, further comprising blanking the sensor data based on the output.

11. The method of any of embodiments 9-10, further comprising flagging a user of the sensor device, on a display interface, based on the output.

12. The method of any of embodiments 9-11, further comprising identifying a resolution associated with the erroneous sensor use condition identified in the sensor data.

13. The method of embodiment 12, further comprising implementing the resolution by manipulating the sensor data, on a display interface, of the sensor device.

14. The method of embodiment 12, further comprising implementing the resolution by manipulating the sensor data received from the sensor device.

15. The method of any of embodiments 9-14, further comprising: receiving input indicating context information relating to the sensor data; inputting the context information relating to the sensor data into the machine learning model; and wherein the output from the machine learning model indicating an erroneous sensor use condition is further based on the context information relating to the sensor data.

16. The method of embodiment 15, wherein the context information relating to the sensor data includes historic information relating to the sensor data over a time period.

17. The method of claim 9, further comprising training the machine learning model to identify the erroneous sensor use conditions based on the sensor data error patterns using the training data comprising the clinical data on the erroneous sensor use conditions.

18. A tangible, non-transitory, machine-readable medium storing instructions that, when executed by a data processing apparatus, cause the data processing apparatus to perform operations comprising those of any of embodiments 1-17.

19. A system comprising: one or more processors; and memory storing instructions that, when executed by the processors, cause the processors to effectuate operations comprising those of any of embodiments 1-17.

20. A system comprising means for performing any of embodiments 1-17.

What is claimed is:

1. A system comprising:

one or more processors; and one or more processor-readable media storing instructions which, when executed by the one or more processors, cause performance of:

obtaining sensor data from a glucose sensor inserted into subcutaneous tissue of a user;

identifying a sensor data error pattern in real time;

identifying an erroneous sensor use condition from two or more different erroneous sensor use conditions that each could cause the sensor data error pattern using a machine learning model;

in response to identifying the erroneous sensor use condition, predicting, using the machine learning model, a resolution from a plurality of possible resolutions that is most effective for resolving the erroneous sensor use condition, wherein the machine learning model was trained with training data comprising pairs of erroneous sensor use conditions and corresponding resolutions, wherein predicting the resolution from the plurality of possible resolutions comprises identifying a possible resolution that is most effective for resolving the erroneous sensor use condition among the plurality of possible resolutions as the predicted resolution;

causing implementation of the resolution;

causing delivery of insulin to the user by an insulin delivery device based on the sensor data manipulated by the implementation of the resolution; and updating a configuration of the machine learning model based on the predicted resolution, an assessment of the predicted resolution, and reference feedback information, wherein the updated configuration is used for future predictions.

2. The system of claim 1, wherein the one or more processor-readable media further store instructions which, when executed by the one or more processors, cause performance of:

blanking display of the sensor data in response to identifying the sensor data error pattern by the machine learning model.

3. The system of claim 1, wherein the one or more processor-readable media further store instructions which, when executed by the one or more processors, cause performance of:

generating an alert informing of the erroneous sensor use condition in response to identifying the erroneous sensor use condition using the machine learning model.

4. The system of claim 1, wherein the implementation of the resolution comprises:

implementing the resolution by manipulating the sensor data via a user interface of a sensor device.

5. The system of claim 1, wherein:

the sensor data includes impedance spectroscopy signals measured at a plurality of signal frequencies using the glucose sensor; and applying the machine learning model comprises generating, from the sensor data that includes the impedance spectroscopy signals, a multi-dimensional feature input to the machine learning model.

6. The system of claim 1, wherein the one or more processor-readable media further store instructions which, when executed by the one or more processors, cause performance of:

obtaining input indicating context information relating to the sensor data; and applying the machine learning model to the context information relating to the sensor data, wherein outputs of the machine learning model are further based on the context information relating to the sensor data.

7. The system of claim 6, wherein the context information relating to the sensor data includes historic information relating to the sensor data over a time period.

8. The system of claim 1, wherein the machine learning model is trained based on clinical data on the erroneous sensor use condition.

9. A processor-implemented method comprising:

obtaining sensor data from a glucose sensor inserted into subcutaneous tissue of a user;

identifying a sensor data error pattern in real time;

identifying an erroneous sensor use condition from two or more different erroneous sensor use conditions that each could cause the sensor data error pattern using a machine learning model;

in response to identifying the erroneous sensor use condition, predicting, using the machine learning model, a resolution from a plurality of possible resolutions that is most effective for resolving the erroneous sensor use condition, wherein the machine learning model was trained with training data comprising pairs of erroneous sensor use conditions and corresponding resolutions, wherein predicting the resolution from the plurality of possible resolutions comprises identifying a possible resolution that is most effective for resolving the erroneous sensor use condition among the plurality of possible resolutions as the predicted resolution;

causing implementation of the resolution;

causing delivery of insulin to the user by an insulin delivery device based on the sensor data manipulated by the implementation of the resolution; and updating a configuration of the machine learning model based on the predicted resolution, an assessment of the predicted resolution, and reference feedback information, wherein the updated configuration is used for future predictions.

10. The processor-implemented method of claim 9, wherein the resolution comprises at least one of:

adjusting a signal of the sensor data;

adding a filter to a signal of the sensor data, adjusting a filter of a signal of the sensor data, replacing a signal of the sensor data;

removing a signal from the sensor data; or replacing the glucose sensor with a replacement glucose sensor.

11. The processor-implemented method of claim 9, further comprising generating an alert informing of the erroneous sensor use condition in response to identifying the erroneous sensor use condition using the machine learning model.

12. The processor-implemented method of claim 9, wherein the implementation of the resolution comprises implementing the resolution by manipulating the sensor data via a user interface of a sensor device.

13. The processor-implemented method of claim 9, wherein:

the sensor data includes impedance spectroscopy signals measured at a plurality of signal frequencies using the glucose sensor; and applying the machine learning model comprises generating, from the sensor data that includes the impedance spectroscopy signals, a multi-dimensional feature input to the machine learning model.

14. The processor-implemented method of claim 9, further comprising:

obtaining input indicating context information relating to the sensor data; and applying the machine learning model to the context information relating to the sensor data, wherein outputs of the machine learning model are further based on the context information relating to the sensor data.

15. The processor-implemented method of claim 14, wherein the context information relating to the sensor data includes historic information relating to the sensor data over a time period.

16. The processor-implemented method of claim 9, wherein the machine learning model is trained based on clinical data on the erroneous sensor use condition.

17. A processor-implemented method comprising:

obtaining sensor data from a glucose sensor inserted into subcutaneous tissue of a user, wherein the glucose sensor includes a single working electrode;

identifying a sensor data error pattern in real time;

identifying an erroneous sensor use condition from two or more different erroneous sensor use conditions that each could cause the sensor data error pattern using a machine learning model;

in response to identifying the erroneous sensor use condition, predicting, using the machine learning model, a resolution from a plurality of possible resolutions that is most effective for resolving the erroneous sensor use condition, wherein the machine learning model was trained with training data comprising pairs of erroneous sensor use conditions and corresponding resolutions, wherein predicting the resolution from the plurality of possible resolutions comprises identifying a possible resolution that is most effective for resolving the erroneous sensor use condition among the plurality of possible resolutions as the predicted resolution;

causing implementation of the resolution;

causing delivery of insulin to the user by an insulin delivery device based on the sensor data manipulated by the implementation of the resolution; and updating a configuration of the machine learning model based on the predicted resolution, an assessment of the predicted resolution, and reference feedback information, wherein the updated configuration is used for future predictions.

18. The processor-implemented method of claim 17, further comprising:

obtaining input indicating context information relating to the sensor data, wherein the sensor data error pattern comprises a low signal error pattern, and wherein the context information comprises historic sensor data over a time period that is used to disambiguate between the two or more different erroneous sensor use conditions comprising temporary signal loss and sensitivity loss.

\* \* \* \* \*